US009918854B2

(12) United States Patent
Bonin, Jr. et al.

(10) Patent No.: US 9,918,854 B2
(45) Date of Patent: Mar. 20, 2018

(54) COMPOUND ANGLE IMPLANT

(75) Inventors: Henry Keith Bonin, Jr., Memphis, TN (US); David Edward Chreene, Hernando, MS (US); Alexander Iwan Seidl, Zurich (CH); Claude Mathieu, Zurich (CH); Daniel Zimmerman, Oberentfelden (CH); Francis X. Mendoza, Purchase, NY (US)

(73) Assignee: Smith & Nephew, Inc., Memphis, TN (US)

( * ) Notice: Subject to any disclaimer, the term of this patent is extended or adjusted under 35 U.S.C. 154(b) by 126 days.

(21) Appl. No.: 14/004,693

(22) PCT Filed: Mar. 15, 2012

(86) PCT No.: PCT/US2012/029180
§ 371 (c)(1),
(2), (4) Date: Apr. 18, 2014

(87) PCT Pub. No.: WO2012/125795
PCT Pub. Date: Sep. 20, 2012

(65) Prior Publication Data
US 2014/0222153 A1 Aug. 7, 2014

Related U.S. Application Data

(60) Provisional application No. 61/453,328, filed on Mar. 16, 2011, provisional application No. 61/475,357, (Continued)

(51) Int. Cl.
*A61F 2/40* (2006.01)
*A61F 2/46* (2006.01)
*A61F 2/30* (2006.01)

(52) U.S. Cl.
CPC .......... *A61F 2/4637* (2013.01); *A61F 2/4014* (2013.01); *A61F 2/4657* (2013.01);
(Continued)

(58) Field of Classification Search
CPC .... A61F 2/4014; A61F 2/4637; A61F 2/4684; A61F 2002/30479; A61F 2002/30538;
(Continued)

(56) References Cited

U.S. PATENT DOCUMENTS 3,694,820 A  10/1972  Scales et al.
3,803,641 A   4/1974  Golyakhovsky
(Continued)

FOREIGN PATENT DOCUMENTS

AZ    8800767    8/1988
CA    1237554    6/1988
(Continued)

OTHER PUBLICATIONS

Authorized officer Jae Cheol Jeong, International Search Report/Written Opinion in PCT/US2012/029180 dated Sep. 25, 2012, 10 pages.
(Continued)

*Primary Examiner* — David H Willse
*Assistant Examiner* — Javier Blanco
(74) *Attorney, Agent, or Firm* — Fish & Richardson P.C.

(57) ABSTRACT

A method of aligning implant components includes placing a first implant component in bone, followed by: coupling a first intermediate member to the first implant component; coupling a first alignment member to the first intermediate member; rotating the members as a unit to place the first intermediate member in an alignment position; removing the first alignment member from the first intermediate member; coupling a second alignment member to a second intermediate member; coupling the second intermediate member to the first intermediate member and rotating the second alignment member and the second intermediate member as a unit relative to the first intermediate member to provide a desired orientation of the second intermediate member. An align-
(Continued)

ment system for aligning first and second members includes a first alignment member having an offset channel dimensioned to receive the first member, and a second alignment member having a channel dimensioned to receive the second member.

26 Claims, 32 Drawing Sheets

Related U.S. Application Data filed on Apr. 14, 2011, provisional application No. 61/491,962, filed on Jun. 1, 2011.

(52) U.S. Cl.
CPC .......... *A61F 2/4684* (2013.01); *A61F 2/4612* (2013.01); *A61F 2002/3054* (2013.01); *A61F 2002/30332* (2013.01); *A61F 2002/30433* (2013.01); *A61F 2002/30474* (2013.01); *A61F 2002/30494* (2013.01); *A61F 2002/30538* (2013.01); *A61F 2002/30616* (2013.01); *A61F 2002/30617* (2013.01); *A61F 2002/4037* (2013.01); *A61F 2002/4638* (2013.01); *A61F 2002/4668* (2013.01); *A61F 2002/4681* (2013.01)

(58) Field of Classification Search
CPC .... A61F 2002/3054; A61F 2002/30617; A61F 2002/4668; A61F 2002/4037
See application file for complete search history.

(56) References Cited

U.S. PATENT DOCUMENTS

| | | | |
|---|---|---|---|
| 3,815,157 A | 6/1974 | Skorecki et al. |
| 3,842,442 A | 10/1974 | Kolbel |
| 3,869,730 A | 3/1975 | Skobel |
| 3,891,998 A | 7/1975 | Lennox |
| 3,916,451 A | 11/1975 | Buechel et al. |
| 3,978,528 A | 9/1976 | Crep |
| 3,979,778 A | 9/1976 | Stroot |
| 4,003,095 A | 1/1977 | Gristina |
| 4,030,143 A | 6/1977 | Elloy et al. |
| 4,040,131 A | 8/1977 | Gristina |
| 4,045,825 A | 9/1977 | Stroot |
| 4,045,826 A | 9/1977 | Stroot |
| 4,106,130 A | 8/1978 | Scales |
| 4,179,758 A | 12/1979 | Gristina |
| 4,261,062 A | 4/1981 | Amstutz et al. |
| 4,355,427 A | 10/1982 | Schneider |
| 4,483,023 A | 11/1984 | Hoffman, Jr. et al. |
| 4,524,467 A | 6/1985 | DeCarlo, Jr. |
| 4,676,797 A | 6/1987 | Anapliotis et al. |
| 4,676,798 A | 6/1987 | Noiles |
| 4,693,723 A | 9/1987 | Gabard |
| 4,851,007 A | 7/1989 | Gray |
| 4,865,605 A | 9/1989 | Dines et al. |
| 4,878,917 A | 11/1989 | Kranz et al. |
| 4,908,032 A | 3/1990 | Keller |
| 4,919,670 A | 4/1990 | Dale et al. |
| 5,002,578 A | 3/1991 | Luman |
| 5,002,581 A | 3/1991 | Paxson et al. |
| 5,080,673 A | 1/1992 | Burkhead et al. |
| 5,080,685 A | 1/1992 | Bolesky et al. |
| 5,314,479 A | 5/1994 | Rockwood et al. |
| 5,458,651 A | 10/1995 | Lawes |
| 5,653,765 A | 8/1997 | McTighe et al. |
| 5,725,592 A | 3/1998 | White et al. |
| 5,755,805 A | 5/1998 | Whiteside |
| 5,961,555 A | 10/1999 | Huebner |
| 6,197,062 B1 | 3/2001 | Fenlin |
| 6,197,063 B1 | 3/2001 | Dews |
| 6,228,120 B1 | 5/2001 | Leonard et al. |
| 6,508,840 B1 | 1/2003 | Rockwood et al. |
| 6,589,282 B2 | 7/2003 | Pearl |
| 6,706,072 B2 | 3/2004 | Dwyer et al. |
| 6,746,487 B2 | 6/2004 | Scifert et al. |
| 6,749,637 B1 | 6/2004 | Bahler |
| 6,793,681 B1 | 9/2004 | Pope et al. |
| 6,818,019 B2 | 11/2004 | Horber |
| 7,097,663 B1 | 8/2006 | Nicol et al. |
| 7,169,184 B2 | 1/2007 | Dalla Pria |
| 7,238,207 B2 | 7/2007 | Blatter et al. |
| 2001/0049561 A1 | 12/2001 | Dews et al. |
| 2001/0053935 A1 | 12/2001 | Hartdegen et al. |
| 2003/0204266 A1 | 10/2003 | Gerbec et al. |
| 2004/0186579 A1* | 9/2004 | Callaway .............. A61F 2/4014 623/19.14 |
| 2004/0199260 A1 | 10/2004 | Pope et al. |
| 2005/0197708 A1 | 9/2005 | Stone et al. |
| 2007/0162140 A1 | 7/2007 | McDevitt |
| 2008/0114461 A1* | 5/2008 | Collazo ................. A61F 2/4014 623/19.14 |
| 2009/0204222 A1 | 8/2009 | Burstein |
| 2009/0312838 A1 | 12/2009 | Klotz |

FOREIGN PATENT DOCUMENTS

| | | |
|---|---|---|
| DE | 3216111 | 11/1983 |
| DE | 3478896 | 8/1989 |
| DE | 29918589 | 9/1999 |
| EP | 127503 | 12/1984 |
| EP | 192181 | 8/1986 |
| EP | 278807 | 8/1988 |
| EP | 299889 | 1/1989 |
| EP | 329854 | 8/1989 |
| EP | 931522 B1 | 3/2004 |
| EP | 1472999 | 3/2004 |
| EP | 1905397 B1 | 11/2011 |
| FR | 2545352 | 11/1984 |
| FR | 2578739 | 9/1986 |
| FR | 2579454 | 10/1986 |
| FR | 2610515 | 8/1988 |
| FR | 2618065 | 1/1989 |
| FR | 2619502 | 2/1989 |
| FR | 2773469 | 1/1998 |
| GB | 2166654 | 5/1986 |
| GB | 2210793 | 6/1989 |
| JP | 2009297515 A | 12/2009 |
| SU | 1152584 | 4/1985 |
| SU | 11279629 | 12/1986 |
| SU | 1286194 | 1/1987 |
| WO | WO 2004030581 A2 * | 4/2004 ........... A61F 2/4014 |

OTHER PUBLICATIONS

Search report of German priority application DE102005054649.8 dated Jun. 26, 2006.
Extended European Search Report for European Application 12758030.6, dated Jul. 30, 2014.
First Office Action for Chinese Application 201280023406.0, dated Apr. 3, 2015.

* cited by examiner

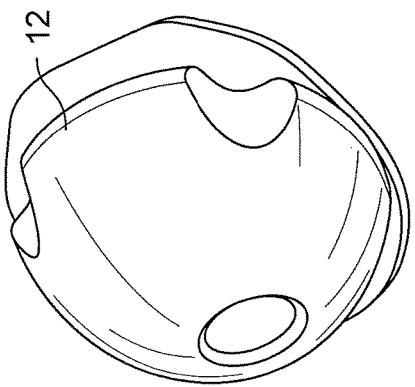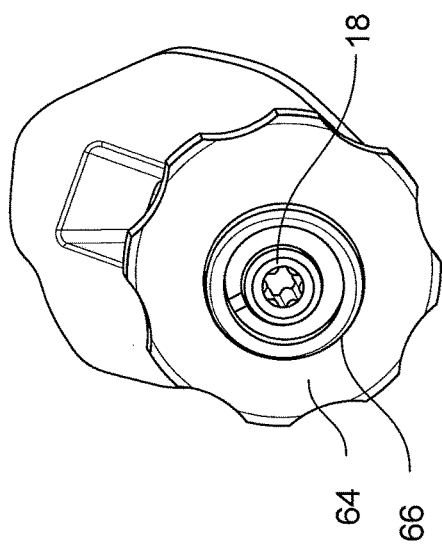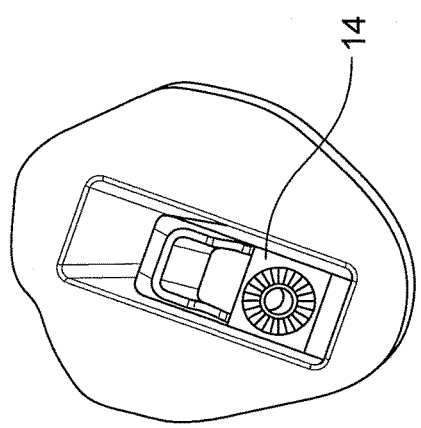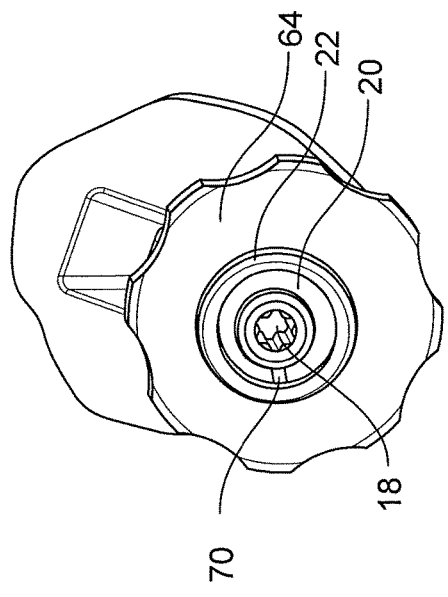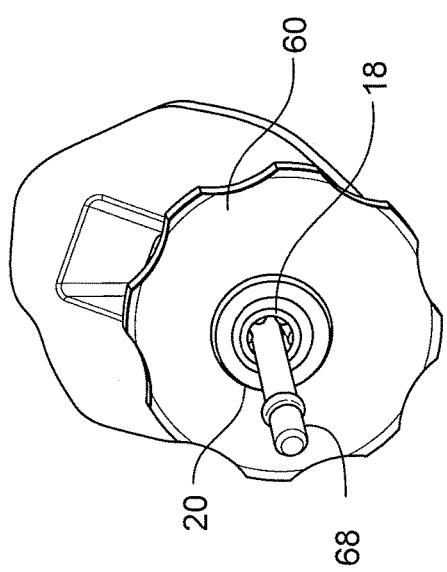

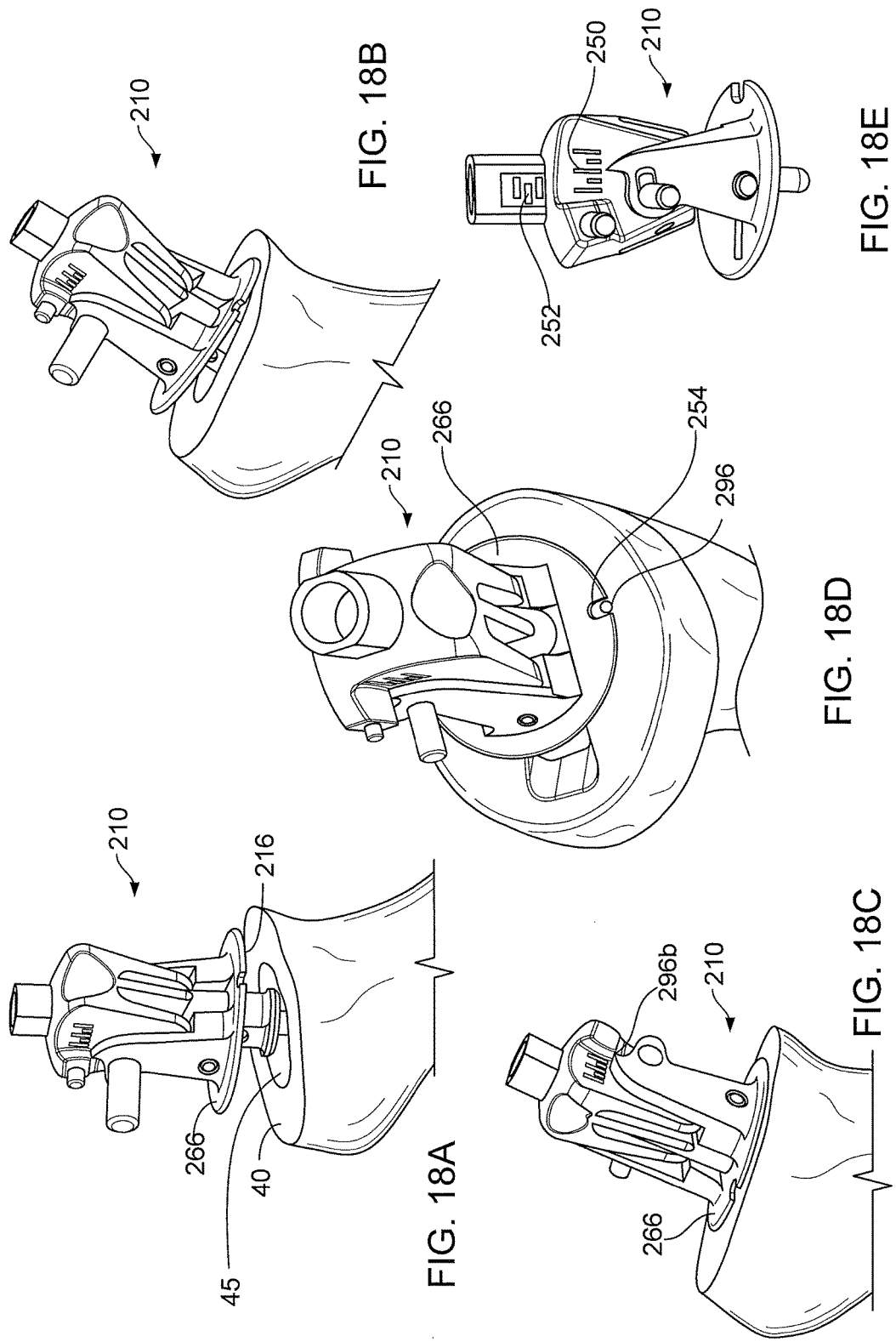

COMPOUND ANGLE IMPLANT

CROSS-REFERENCE TO RELATED APPLICATION

This application claims priority to and the full benefit of U.S. Provisional Application Ser. No. 61/453,328, filed Mar. 16, 2011, and titled "Compound Angle Guide," U.S. Provisional Application Ser. No. 61/475,357, filed Apr. 14, 2011, and titled "Compound Angle Implant," and U.S. Provisional Application Ser. No. 61/491,962, filed Jun. 1, 2011, and titled "Compound Angle Implant," the entire contents of which are incorporated herein by reference.

TECHNICAL FIELD

This invention relates to a compound angle implant.

BACKGROUND

During joint replacement surgery, an implant is inserted into or attached to a bone that has been prepared to receive the implant. To simulate native anatomy during joint replacement surgery, it is known to provide the surgeon with modular, adjustable implant components. Modular, adjustable implant components can allow the surgeon to accommodate a large range of joint and bone configurations in patients without, for instance, having to maintain a large inventory of variously configured implant structures.

SUMMARY

During joint replacement surgery, for example, in the shoulder, it is desirable to permit the surgeon to place the stem of the implant into the humeral bone without regard to the orientation of the humeral osteotomy. After placing the stem into the humeral bone, the surgeon selects an implant component that couples to the stem and is configured to anatomically orient the head of the shoulder implant. An inclination-retroversion guide aids the surgeon in selecting the implant component and provides the surgeon with the choice of measuring inclination and/or retroversion.

According to one aspect, a method of aligning first and second implant components includes placing the first implant component in bone, followed by: coupling a first intermediate member to the first implant component; coupling a first alignment member to the first intermediate member; rotating the first alignment member and the first intermediate member as a unit to place the first intermediate member in an alignment position; securing the first intermediate member to the first implant component with the first intermediate member in the alignment position; removing the first alignment member from the first intermediate member; and coupling a second intermediate member to the first intermediate member and rotating the second intermediate member relative to the first intermediate member to provide a desired orientation of the second intermediate member.

Implementations of this aspect may include one or more of the following features. The first alignment member is coupled to the first intermediate member without rotationally aligning the first alignment member relative to the first intermediate member. The first intermediate member includes an indicia. The first alignment member includes a plurality of indicia. The method includes fixing the second intermediate member to the first intermediate member with the second intermediate member in the desired orientation. The method includes coupling a second alignment member to the second intermediate member to rotate the second intermediate member. The second alignment member is coupled to the second intermediate member without rotationally aligning the second alignment member and the second intermediate member. The second intermediate member is in the desired orientation when the second alignment member is parallel to a bone osteotomy. The first intermediate member is in the alignment position when the first alignment member is parallel to a bone osteotomy. The method includes coupling the second member to the second implant component.

According to another aspect, an alignment system for aligning first and second members of an implant connector includes a first alignment member having an outer surface for grasping by a user and a channel dimensioned to receive the first member, the channel extending non-transversely through the first alignment member; and a second alignment member having an outer surface for grasping by a user and a channel dimensioned to receive the second member.

Implementations of this aspect may include the second alignment member channel extending transversely through the second alignment member.

According to another aspect, a method of aligning first and second implant components includes coupling a first intermediate member to the first implant component, coupling an alignment member to the first intermediate member with indicia on the alignment member and indicia on the first intermediate member aligned, rotating the alignment member and the first intermediate member as a unit to an alignment position by aligning indicia on the alignment member with indicia on bone in which the first implant component is received, securing the first intermediate member to the first implant component with the first intermediate member in the alignment position, removing the alignment member from the first intermediate member, and coupling a second intermediate member to the first intermediate member and rotating the second intermediate member relative to the first intermediate member to provide a desired orientation of the second intermediate member.

Implementations of this aspect may include one or more of the following features. The method includes fixing the second intermediate member to the first intermediate member with the second intermediate member in the desired orientation. The method includes coupling the alignment member to the second intermediate member to rotate the second intermediate member. The second intermediate member is in the desired orientation when the alignment member is parallel to a bone osteotomy. The indicia on the alignment member for aligning with the first intermediate member is different from the indicia on the alignment member for aligning with the bone indicia. The method includes coupling the second intermediate member to the second implant component.

According to another aspect, an alignment system for aligning first and second members of an implant connector includes an alignment member having an outer surface for grasping by a user and first and second co-axial channels. The first channel is dimensioned to receive the first member and the second channel is dimensioned to receive the second member. The first channel has an undulating perimeter. The alignment member includes indicia visible to a user for aligning the first member with a bone osteotomy.

Implementations of this aspect may include one or more of the following features. The alignment system includes an impaction tool having an undulating outer perimeter matching the first channel undulating perimeter for receipt within the first channel to contact the second member when the second member is received within the second channel.

According to another aspect, an anatomic guide includes a first member, and a second member coupled to the first member such that the second member can slide and tilt relative to the first member. The second member includes a surface for contacting a bone osteotomy such that with the surface in contact with the bone osteotomy, the relative sliding and tilting of the second member relative to the first member identifies an anatomic implant for use with the osteotomy.

Implementations of this aspect may include one or more of the following features. The guide includes indicators that identify the anatomic implant. The first member is a shaft. The second member is coupled to the shaft to be slidable along the shaft and tiltable relative to the shaft. The second member is a handle gage having first and second portions, the first portion being tiltable relative to the second portion and the first member.

The indicators include indicia that identify the relative tilt of the first portion. The indicators include indicia that identify the relative sliding of the second member. The indicators include a formation on the second member for use in indicating on the osteotomy a rotational alignment of the guide relative to the osteotomy.

The indicators include indicia that identify the relative tilt of the second member, indicia that identify the relative sliding of the second member, and a formation on the second member for use in indicating on the osteotomy a rotational alignment of the guide relative to the osteotomy.

The second member is coupled to the first member to tilt along more than one plane. The second member is coupled to the first member to rotate relative to the first member.

According to another aspect, a method of selecting an implant component, includes coupling a guide to an implant, the guide having a first member and a second member; sliding the second member relative to the first member toward a bone osteotomy; rotating at least a portion of the guide relative to the implant; tilting the second member relative to the first member to orient the guide relative to the osteotomy; and using the orientation of the guide to aid in selecting an implant component.

According to another aspect, a method of aligning first and second implant components includes aligning indicia on first and second intermediate members by relative rotation of at least one of the intermediate members, coupling the first and second intermediate members, coupling the first member to the first implant component, and coupling the second member to the second implant component.

Implementations of this aspect may include one or more of the following features. The first and second intermediate members are aligned before being coupled. The first member is coupled to the first implant prior to aligning the indicia. The first and second members are aligned and coupled before the members are coupled to the implant components. The indicia on the first and second members are aligned with indicia on bone in which one of the implant components is received. The second member is coupled to the second implant after aligning the indicia. The first implant component is a shoulder stem. The second implant component is a shoulder head.

According to another aspect, a method of aligning first and second implant components includes placing the first implant component in bone, marking indicia on the bone, coupling a first intermediate member to the first implant component with indicia on the first intermediate member aligned with the indicia on the bone, coupling a second intermediate member to the first intermediate member with indicia on the second intermediate member aligned with indicia on the first intermediate member, and coupling the second intermediate member to the second implant component.

Implementations of this aspect may include one or more of the following features. The first intermediate member is coupled to the first implant component prior to coupling the second intermediate member to the first intermediate member. Alternatively, the second intermediate member is coupled to the first intermediate member prior to coupling the first intermediate member to the first implant component.

According to another aspect, a connector for attaching first and second implant components includes a first member, a second member, and an interface. The first member is configured to be coupled to the first implant component. The interface is configured to couple the first member to the first implant component. The first member has a male taper angularly offset relative to an axis of rotation of the first member. The second member has a female taper for receiving the male taper. The female taper matches the male taper such that an axis of rotation of the second member is not aligned with the axis of rotation of the first member. The second member has a male taper that is angularly offset relative to the axis of rotation of the second member. The male taper of the second member is configured to couple the second member to the second implant component such that an axis of rotation of the second implant component is not aligned with the axis of rotation of the second member.

Implementations of this aspect may include one or more of the following features. The first member offset is at an angle A and the second member offset is at an angle B such that relative rotation of the first and second members produces an offset angle up to A+B. The first member is configured to be rotatable relative to the first implant component when coupled thereto.

The details of one or more implementations of the invention are set forth in the accompanying drawings and the description below. Other features, objects, and advantages of the invention will be apparent from the description and drawings, and from the claims.

DESCRIPTION OF DRAWINGS

FIGS. 9A-9E illustrate an example technique for using the alignment members of FIG. 8.

FIGS. 18A-18E illustrate the use of the guide of FIG. 15 for determining parameters for the connector.

DETAILED DESCRIPTION

Figure 1:
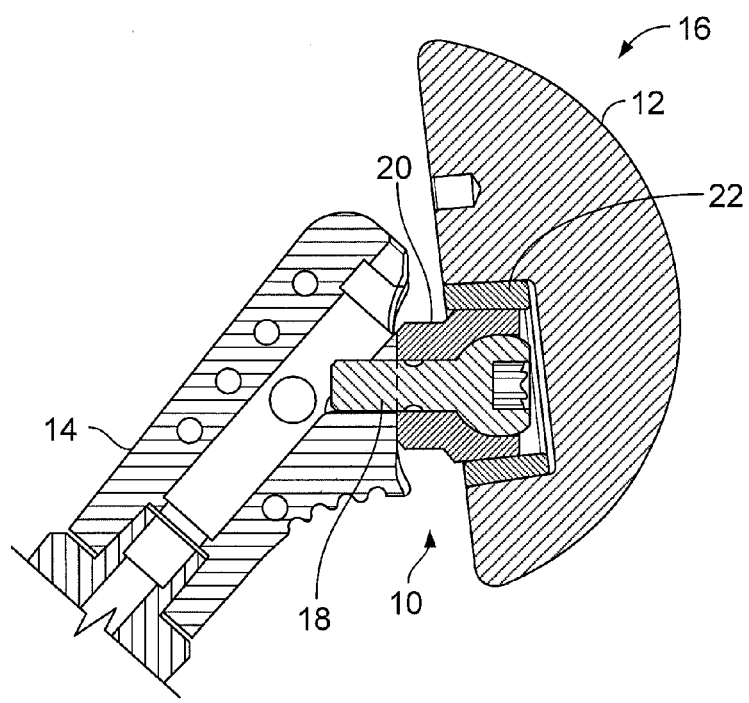
FIG. 1 is a cross-sectional side view of a connector coupling two implants.

Referring to FIG. 1, a connector 10 permits intra-operative adjustment of the inclination and/or retroversion of a second implant component relative to a first implant component, for example, adjustment of a humeral head implant 12 relative to a stem 14 of a prosthesis 16 during shoulder arthroplasty. The adjustment can be made in infinite steps with a maximum angulation of, for example, about +/−20°, with the illustrated implementation showing a maximum angulation of +/−12°. The connector 10 includes a first intermediate member 20 that an surgeon fixes to the stem 14 with an interface, for example, a fixation member such as a screw 18 or a taper or snap-in interface, and a second intermediate member 22 that the surgeon fixes to the head implant 12 via, for example, a tapered press fit.

The stem 14 can be attached to bone by distal fixation, and the connector 10 can be coupled to the stem 14 after the stem 14 is fixed in the bone. The stem 14 can be modular, having proximal portions provided in different lengths that the surgeon can choose from, with the proximal portion being rotatable relative to a distal portion of the stem prior to being fixed in position relative to the distal portion.

Figure 2:
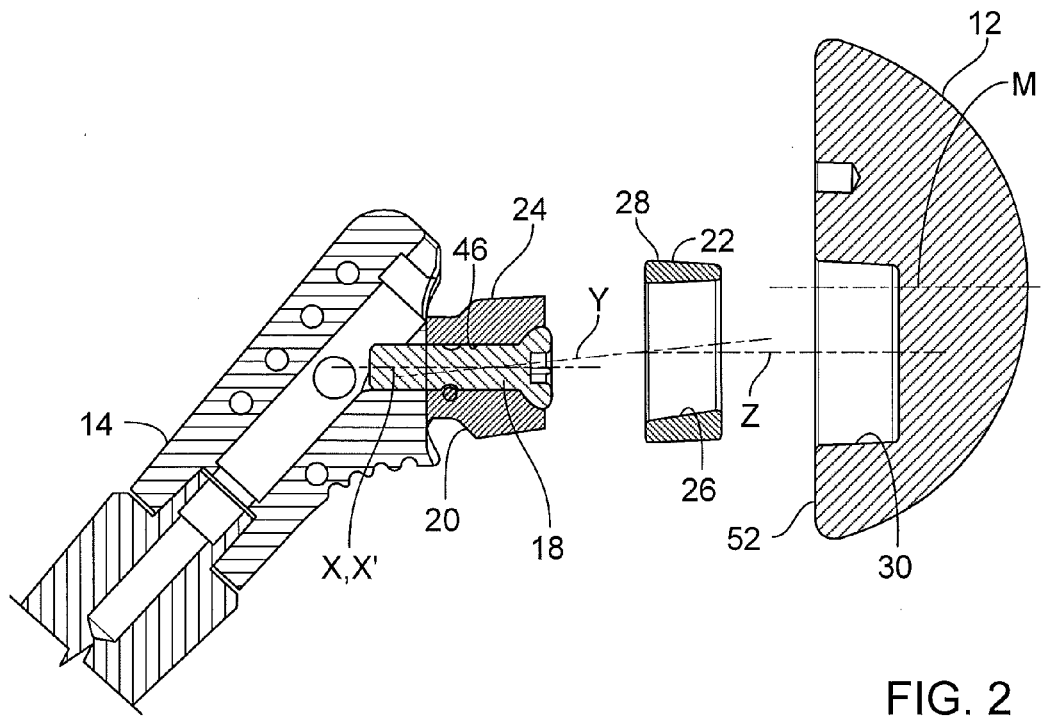
FIGS. 2 and 3 are exploded views of the connector and implants.
Figure 3:
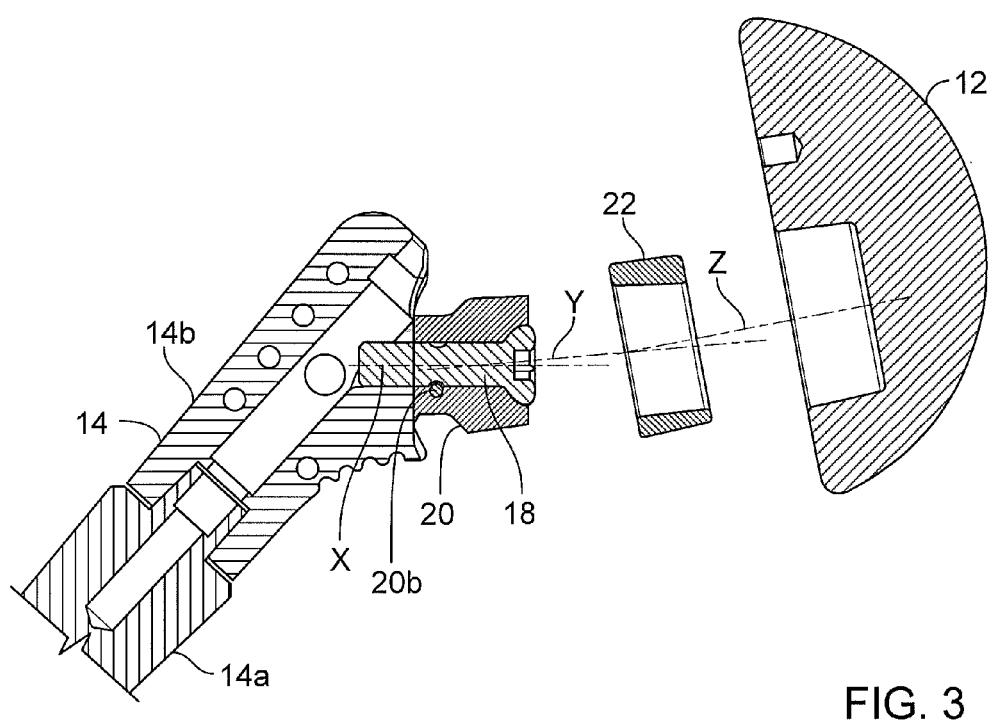

Prior to being fixed to the stem 14, the first member 20 can be coupled to the stem 14 by the screw 18 or other interface to be rotatable relative to the stem 14. Referring to FIGS. 2 and 3, the first member 20 has a male taper 24 that is angularly offset relative to an axis of rotation, X, of the first member. The second member 22 has a female taper 26 for receiving the male taper 24. The female taper 26 matches the male taper 24 such that an axis of rotation, Y, of the second member 22 is not aligned with the axis of rotation, X, of the first member 20. The second member 22 also has a male taper 28 that is angularly offset relative to the axis of rotation, Y, of the second member 22. The male taper 28 of the second member 22 is received by a female taper 30 in the head implant 12 to couple the second member 22 to the head implant 12 such that an axis of rotation, Z, of the head implant 12 is not aligned with the axis of rotation, Y, of the second member 22.

Figure 4A:
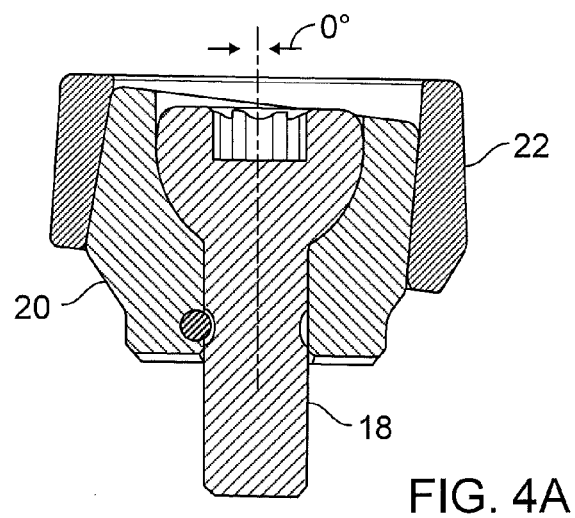
FIGS. 4A-4C are cross-sectional side views of the connector.
Figure 4B:
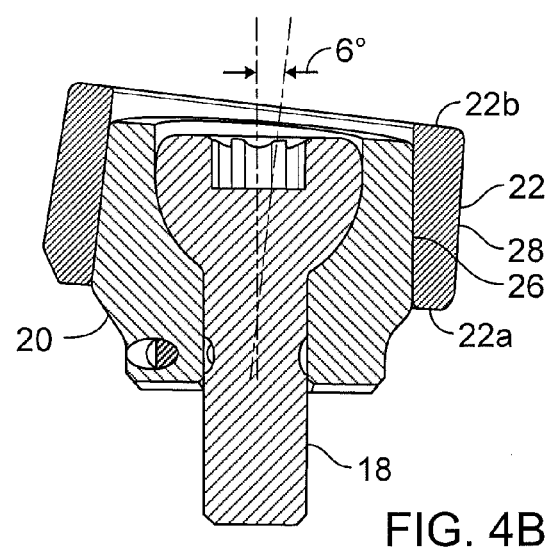
Figure 4C:
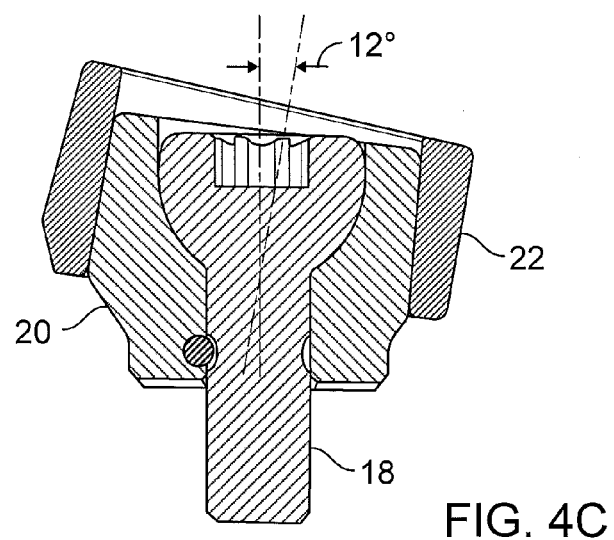

The relative rotary position of the first and second members 20, 22 determines the ultimate angular offset between axes X and Z. For example, in FIG. 2, the first and second members 20, 22 are positioned with the tapers 24 and 28 cancelling each other such that the axes X and Z are parallel. In FIG. 3, the first and second members 20, 22 are positioned with the tapers 24 and 28 being additive with the axes X and Z at their maximum offset angulation. In the illustrated implementation, axes X and Y are offset by an angle, A, for example, 6°, and axes Y and Z are also offset by and angle, B, for example, 6°, such that the maximum offset angulation is A+B, 12°. FIG. 3 shows a +12° angulation. A −12° angulation can be obtained by rotating both of the first and second members 20, 22 by 180°. FIGS. 4A-4C illustrate 0°, 6° and 12° offset angulations of the first and second members 20, 22. Rather than the plus and minus angles being in the inclination plane, as illustrated, the plus/minus angles could be anterior/posterior (version plane).

The axis of rotation, Z, of the female taper 30 in the head implant 12 is offset relative to an axis of symmetry, M, of the head implant 12 such that rotation of the head implant 12 relative to the second member 20 about the axis of rotation, Z, provides another degree of freedom in adjusting the relative position of the stem and head.

Figure 5A:
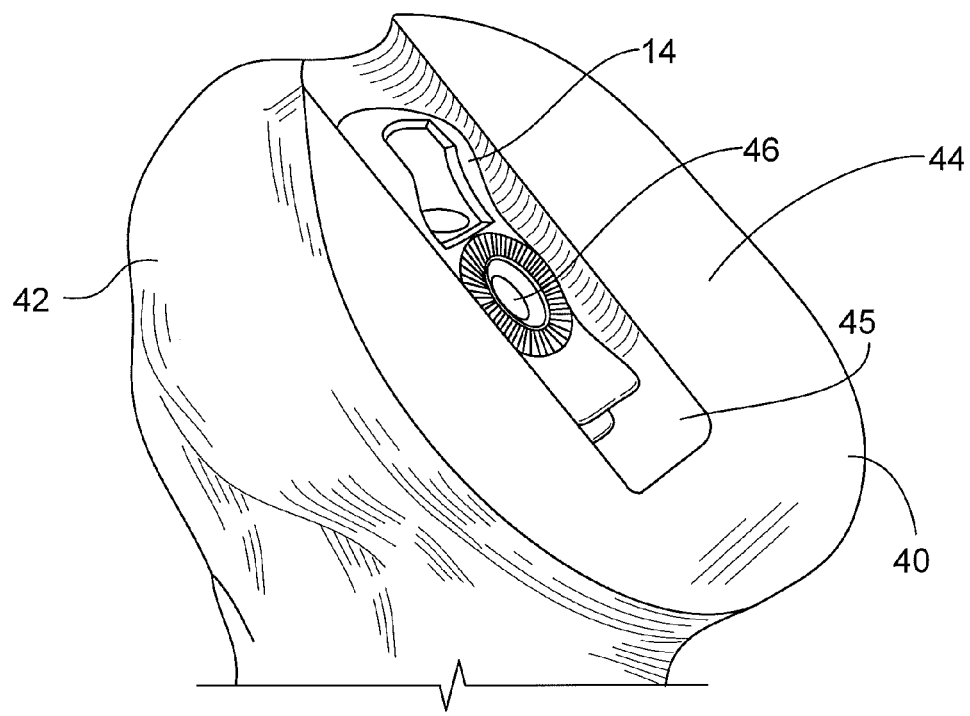
FIGS. 5A and 5B illustrate the orientation of a stem in a humeral bone.
Figure 5B:
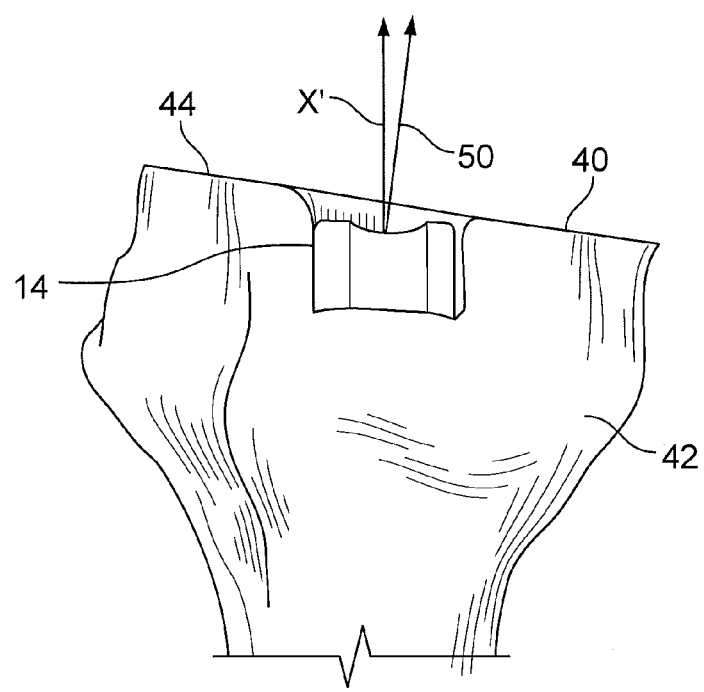
Figure 6A:
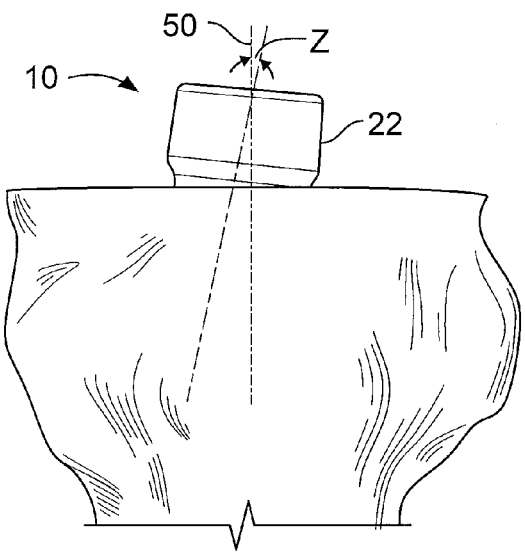
FIGS. 6A-6C illustrate the connector coupled to the implant in the bone.
Figure 6B:
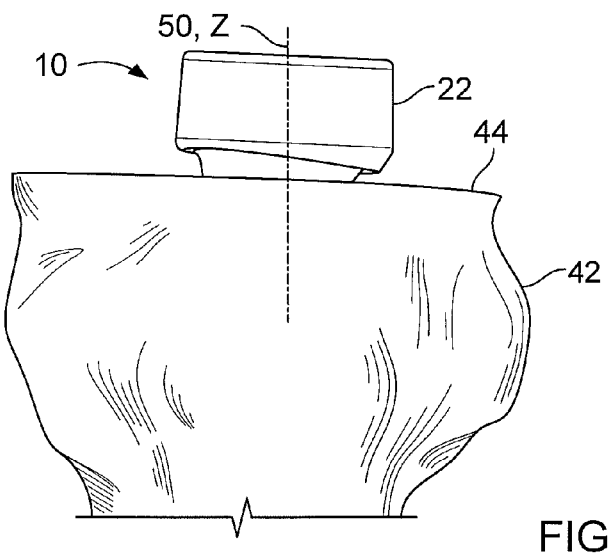
Figure 6C:
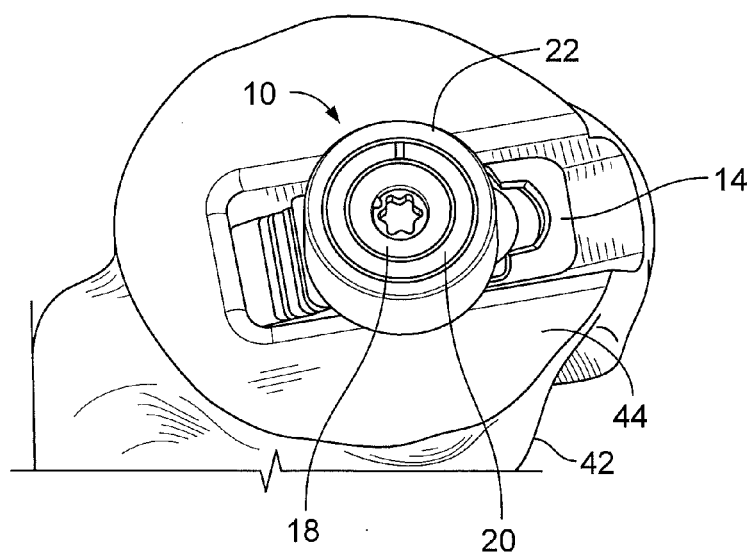

Referring to FIGS. 5A and 5B, during a shoulder arthroplasty procedure, the surgeon typically creates an osteotomy 40 in the humeral bone 42 to form a flat bone surface 44, and bores a channel 45 in the bone 42 to receive the stem 14. The stem 14 has an interface axis, X' (FIG. 2), defined, for example, by a threaded hole 46 that receives screw 18, that coincides with the axis of rotation, X, of the first member 20 when the first member 20 is coupled to the stem 14. However, the axis, X', may not be parallel to a normal vector 50 of the bone surface 44. As illustrated in FIGS. 6A and 6B, the surgeon can intra-operatively adjust the position of the head implant 12 relative to the bone surface 44, for example, to make a surface 52 (FIG. 2) of the head implant 12 parallel to the bone surface 44 (and thus axis, Z, parallel to vector 50), by adjusting the relative rotational position of members 20, 22 from the offset position of FIG. 6A to the parallel position of FIG. 6B. The connector 10 as coupled to stem 14 can be seen in FIG. 6C.

Figure 7A:
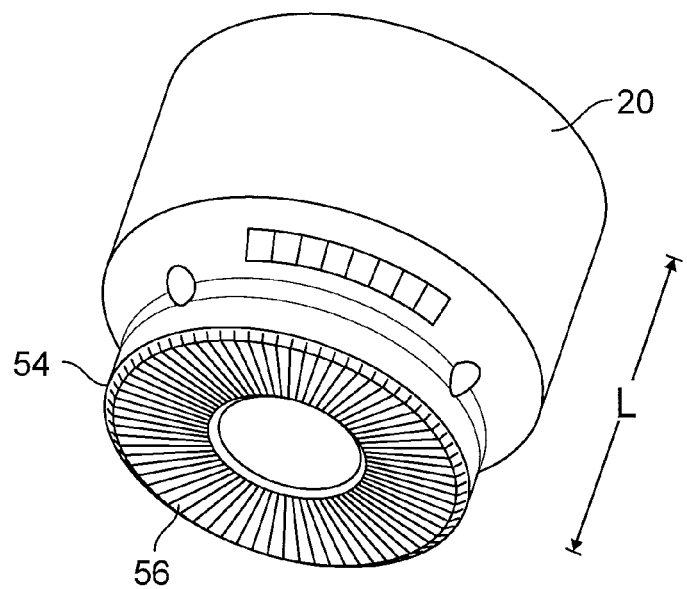
FIGS. 7A and 7B are each perspective views of a member of the connector.
Figure 7B:
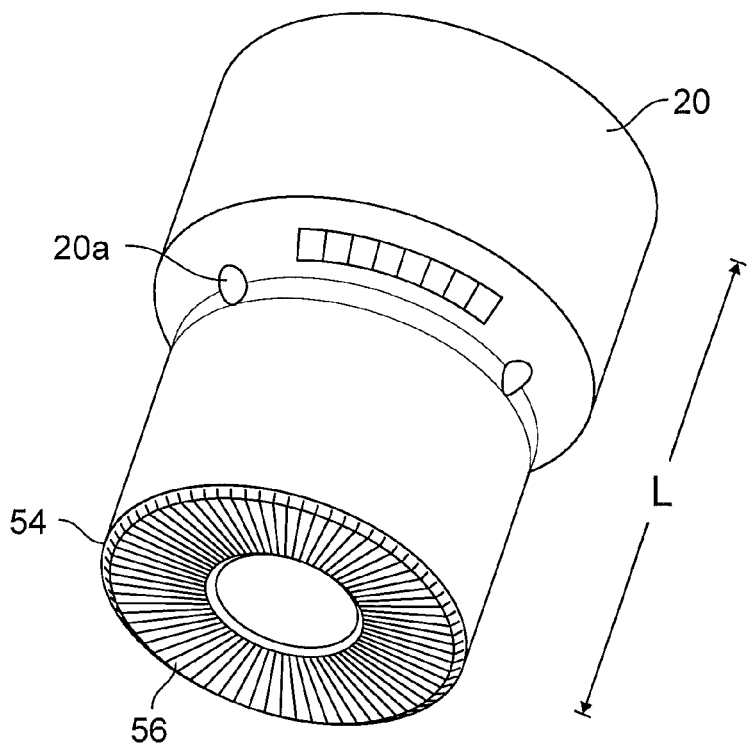
Figure 8A:
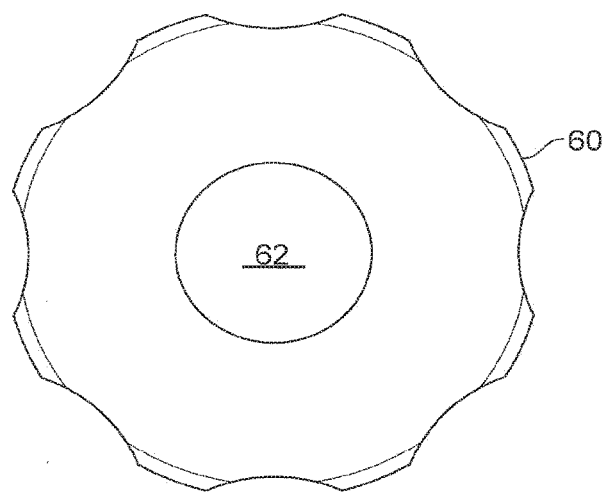
FIGS. 8A and 8B are top and side views of an alignment member for a first member of the connector.
Figure 8B:
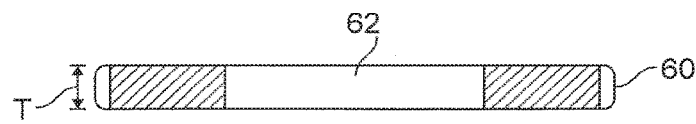
Figure 8C:
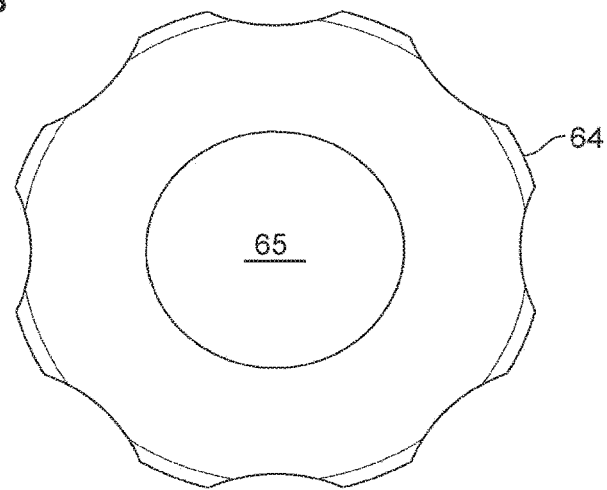
FIGS. 8C and 8D are top and side views of an alignment member for a second member of the connector.
Figure 8D:

The distance between surfaces 44 and 52 is determined by the length of the members 20, 22. The surgeon can set the distance by, for example, selecting among members 20 having a range of lengths, L (FIGS. 7A and 7B). As illustrated in FIGS. 7A and 7B, the member 20 has a stem contacting surface 54 with circumferential ridges 56 that mate with corresponding ridges on the stem 14 to aid in holding the rotational alignment of the member 20 and the stem 14.

Referring to FIGS. 3 and 7B, the member 20 defines pin holes 20*a* that receives pins 20*b* that act to hold the screw 18 within the member 20. The member 20, the pin 20*b*, and the screw 18 can be provided to the surgeon as a preattached assembly. Referring to FIG. 4B, in the illustrated implementation of the member 22, a surface 22*a* of the member 22 is perpendicular to the female taper 26, and a surface 22*b* of the member 22 is perpendicular to the male taper 28.

As discussed above, the surgeon can make the surface 52 of the head implant 12 parallel to the bone surface 44 by adjusting the relative rotational position of members 20, 22 of the connector 10. For example, referring to FIGS. 8A-8D, a first alignment member 60 defines a bore 62 sized to receive the first member 20 in frictional engagement, and a second alignment member 64 defines a bore 65 sized to receive the second member 22 in frictional engagement. The bores 62, 65 extend transversely through the respective alignment members 60, 64. The alignment members 60, 64 are relatively thin, for example, having a thickness, T, of about 6 mm or less, preferably about 3.5-4.5 mm, and are transparent, made from, for example, polyetherimide, to facilitate alignment of the first and second member 20, 22, as discussed below.

The alignment members 60, 64 can be used to attach the first and second members 20, 22 to the stem 14 without the need for additional angle guides or markings on the bone, as will be discussed further below. Referring to FIGS. 9A-9E, an example method of using the alignment members 60, 64 includes creating a bone resection of the humeral head and implanting the stem 14 into the broached cavity of the bone using distal fixation (FIG. 9A). The surgeon then places the alignment member 64 about a pre-assembled trial connector having attached first and second trial members 66. The attached first and second trial members 66 can be tilted relative to each other but rotate as a unit. The surgeon screws the alignment member 64/trial members 66 assembly onto the stem 14, and rotates the alignment member 64 and the pre-assembled trial connector as an unit about the screw axis until the user perceives by sight and feel that the alignment member 64 is parallel to the osteotomy face (FIG. 9B). The user then tightens the screw 18. The trial phase of the procedure is completed by attaching the humeral trial head 12 (FIG. 9C) and testing the trial implant to determine if the connector length is appropriate. The trial phase determines the desired length of the first member 20 and determines whether the osteotomy angle can be corrected with the range provided by the first and second members 20, 22.

The surgeon then selects the first member 20 according to the length of the trial connector, and partially screws the first member 20 to the stem 14 using a tool 68. The surgeon uses the alignment member 60 press fit over the first member 20 to rotate the first member 20 until the surgeon perceives that the alignment member 60 is parallel to the osteotomy face (FIG. 9D) by looking through the alignment member 60 or by judging the parallelism via side viewing. The alignment member 60 is press fit over the first member 20 without the need for rotationally aligning the alignment member 60 and the first member 20. The surgeon then tightens the screw to fix the first member 20 to the stem and removes the alignment member 60. The surgeon then press-fits the alignment member 64 over the second member 22 and places the second member 22 over the first member 20 and uses the alignment member 64 to rotate the second member 22 relative to the first member 20 until the surgeon perceives that the alignment member 64 is parallel to the osteotomy face (FIG. 9E) by looking through the alignment member 64. The alignment member 64 is press fit over the second member 22 without the need for rotationally aligning the alignment member 64 and the second member 20. If the above steps do not provide the desired result, the surgeon can loosen the screw, rotate the first member 20 90 degrees for example, with reference to a marking 70 on the first member 20, tightens the screw, and then re-align the second member 22 using the alignment member 64.

Figure 10A:
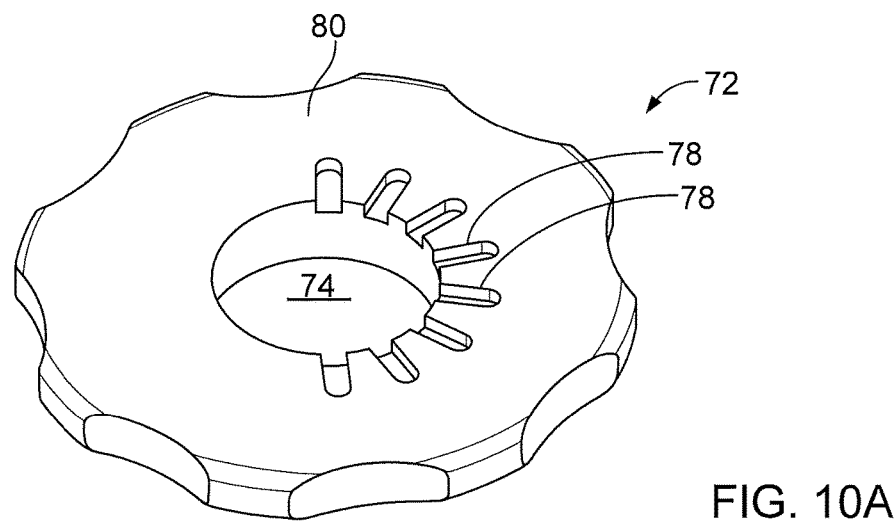
FIGS. 10A and 10B are top and side view of an alternative implementation of an alignment member for the first member of the connector.
Figure 10B:
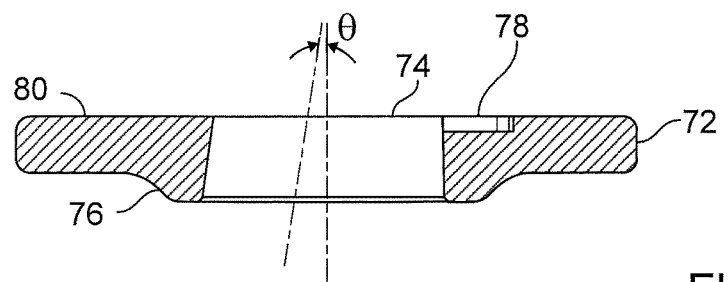
Figure 10C:
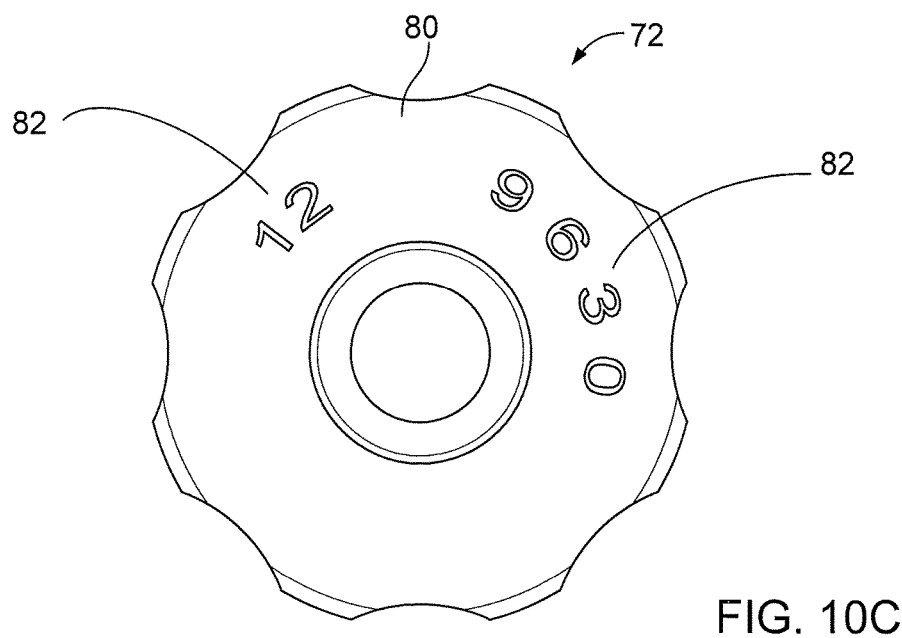
FIG. 10C is a top view of the alignment member from FIG. 10A with alternative indicia.

Referring to FIGS. 10A and 10B, an alignment member 72 defines a bore 74 sized to receive the first member 20 in frictional engagement. The bore 74, rather than extending transversely through the alignment member, as in the implementations described above, is offset at an angle, θ, in the range of, for example, four to six degrees, for reasons discussed below. The alignment member 72 includes a region 76 of increased thickness to facilitate manufacturing, and can also include a plurality of indicia 78 on the top surface 80. Alternatively, the top surface 80 can include indicia 82 as shown in FIG. 10C, the indicia 82 corresponding to, for example, a total angular range of the connector 10.

Rather than using the alignment member 60 with the first member 20, the alignment member 72 having an offset bore can be used. Without the use of an offset bore, as in the alignment member 60, it is possible that, due to the six degree offset of the second member 22, after alignment of the first member 20, the alignment member 64 with the second member 22 cannot be aligned parallel to the osteotomy face. However, if the bore is offset, for example, by 4 degrees, any error is distributed increasing the likelihood of parallel alignment. To minimize any error, the surgeon can use the alignment member 72 having a six degree offset, which simulates the second member 22, and indicia 82.

Figure 11A:
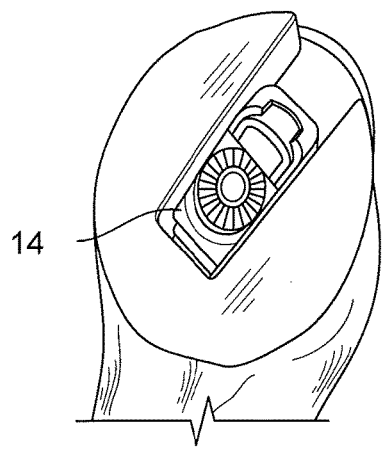
FIGS. 11A-11D illustrate an example technique for using the alignment members of FIGS. 8 and 10.
Figure 11B:
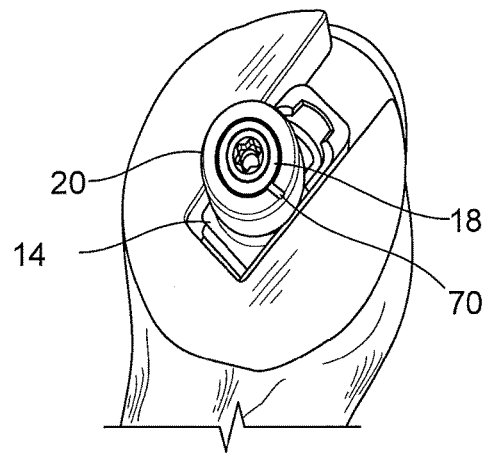
Figure 11C:
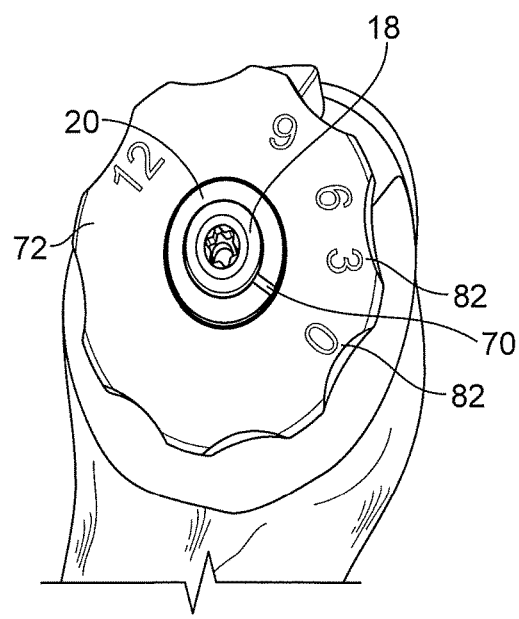
Figure 11D:
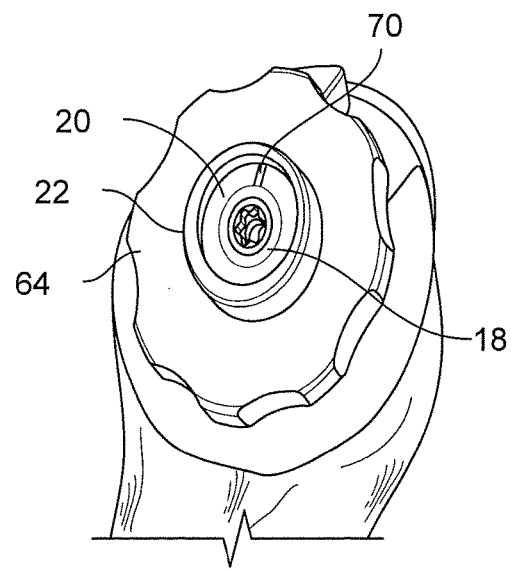

Referring to FIGS. 11A-11D, an example method of using the alignment members 72, 64 includes creating a bone resection of the humeral head and implanting the stem 14 into the broached cavity of the bone using distal fixation (FIG. 11A). The surgeon then selects the first member 20 having the appropriate length, for example, determined according to the length of the trial connector, and partially screws the first member 20 to the stem 14 (FIG. 11B). The first member 20 is provided with a single indicia 70 that the surgeon aligns with one of the alignment member indicia 78, 82 of the alignment member 72 when placing the alignment member 72 onto the first member 20 (FIG. 11C). Thus aligned, the surgeon rotates the alignment member 72 with the first member 20 to see if the alignment member 72 can be positioned parallel to the osteotomy face. The surgeon progresses through the plurality of indicia 78, 82 on the alignment member 72 until the surgeon perceives that the alignment member 72 is parallel to the osteotomy. If the alignment member 72 is parallel to the osteotomy, then the alignment member 64 with the second member 22 can likewise be positioned parallel to the osteotomy. The surgeon then tightens the screw 18 to fix the first member 20 to the stem and removes the alignment member 72. The surgeon then press-fits the alignment member 64 over the second member 22 and places the second member 22 over the first member 20. The surgeon uses the alignment member 64 to rotate the second member 22 relative to the first member 20 until the surgeon perceives that the alignment member 64 is parallel to the osteotomy face (FIG. 11D). The alignment member 64 is press fit over the second member 22 without the need for rotationally aligning the alignment member 64 and the second member 20.

Figure 12A:
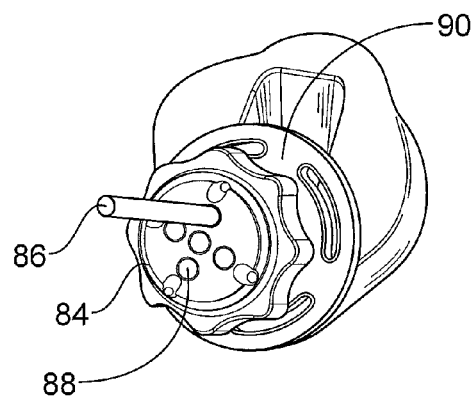
FIGS. 12A-13B illustrate various techniques for using the alignment members of FIGS. 8 and 10.
Figure 12B:
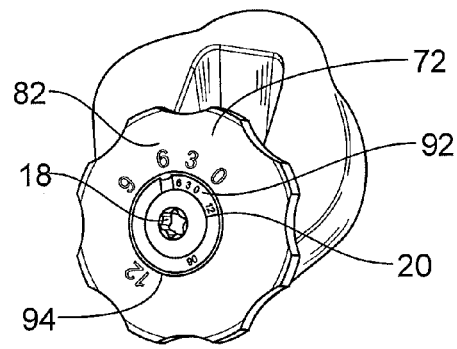

Referring to FIGS. 12A and 12B, in an alternative technique, a modified angle guide 84 is used to facilitate alignment of the first and second members 20, 22. After the trial phase, a rod 86 is fixed in line with the threaded, screw receiving hole of the stem 14. The angle guide 84, having single or multiple through holes 88 each set at an angle to a distal disc part 90 of the guide 84, for example, five holes at 0°, 3°, 6°, 9°, and 12°, is slid over the rod 86 and against the bone osteotomy, with the rod extending through one of the holes 88. The guide 84 is rotated about the axis of the rod to find the angle which best matches the distal disc surface 90 of the guide 84 to the bone osteotomy. The rod 86 can be slid through different holes 88 until the best angle match is found. The value of the angle is marked as a digit on the guide 84.

Referring particularly to FIG. 12B, in this technique the first member 20 and the alignment member 72 each include angle indicia 92, 82, respectively. In addition, the alignment member 72 has a 6° eccentric bore 94. In use, the first member 20 and the alignment member 72 are aligned at the same digit as determined by the guide 84. The surgeon then rotates the alignment member 72 and the first member 20 until the alignment member 72 is perceived to be parallel to the osteotomy. The surgeon then employs the second alignment member 64, as described above.

Figure 13A:
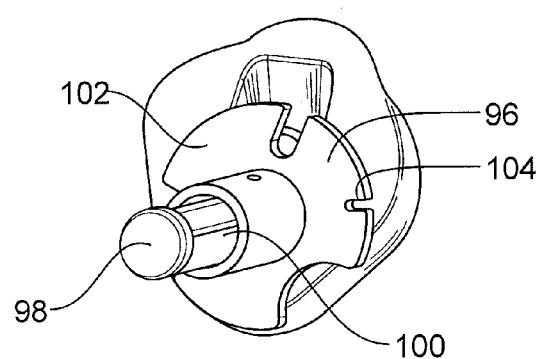
Figure 13B:
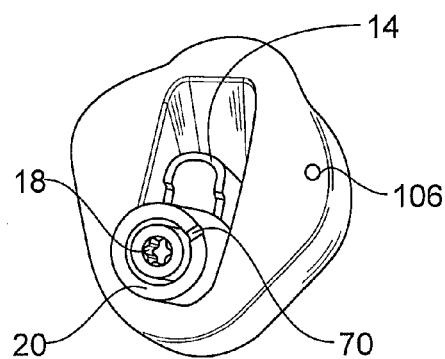

Referring to FIGS. 13A and 13B, in an alternative technique, a set of modified angle guides 96 are used to facilitate alignment of the first and second members 20, 22. After the trial phase, a rod 98 is fixed in line with the threaded, screw receiving hole of the stem 14. Each angle guide 96 has a different, single through hole 100 set at an angle to a distal disc part 102 of the guide 96, for example, five guides each with a holes at 0°, 3°, 6°, 9°, or 12°. Each angle guide 96 in turn is slid over the rod 98 and against the bone osteotomy, with the rod extending through the hole 100. The guide 96 is rotated about the axis of the rod to find the angle which best matches the distal disc surface 102 of the guide 96 to the bone osteotomy. The rod 98 is slid through different guides 96 until the best angle match is found. The guides 96 each have an indicia 104, and when the best fit is determined, the indicia of the best fit guide is transferred to the bone resection as a mark 106 on the osteotomy.

Figure 19A:
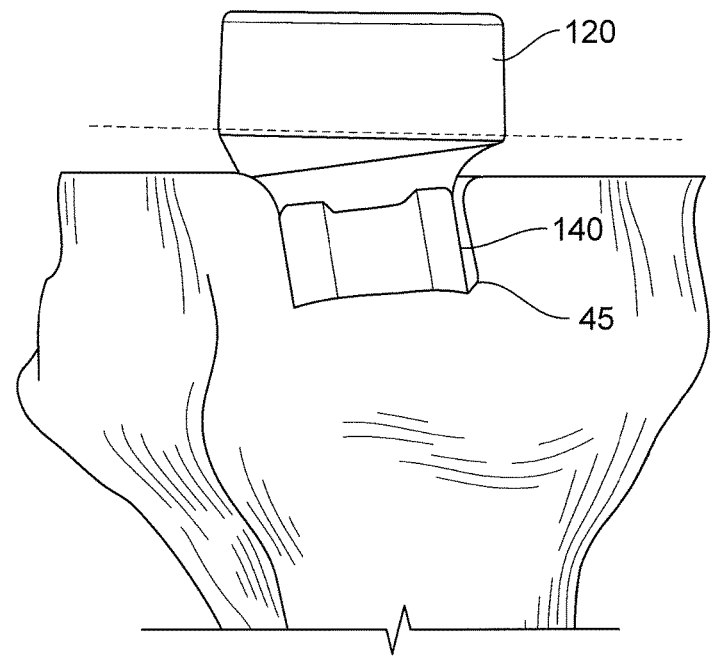
FIGS. 19A and 19B illustrate a selected implant component.
Figure 19B:
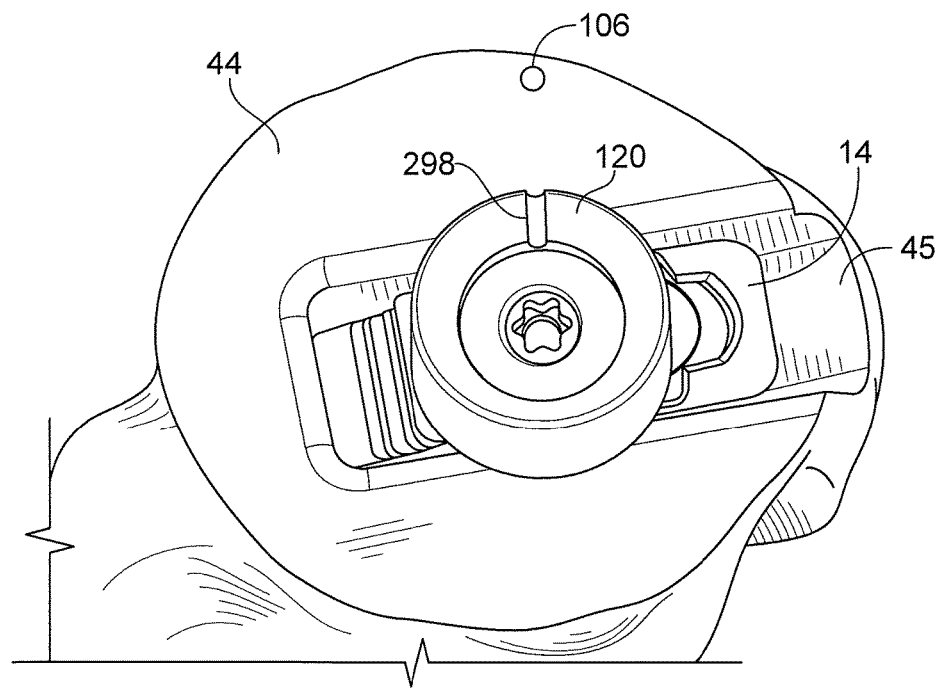

A first member 20 having an indicia 70 is attached to the stem 14 using the screw 18, with the indicia 70 on the first member 20 aligned with the osteotomy mark 106 (FIG. 19B). The surgeon then employs the second alignment member 64, as described above.

Figure 14A:
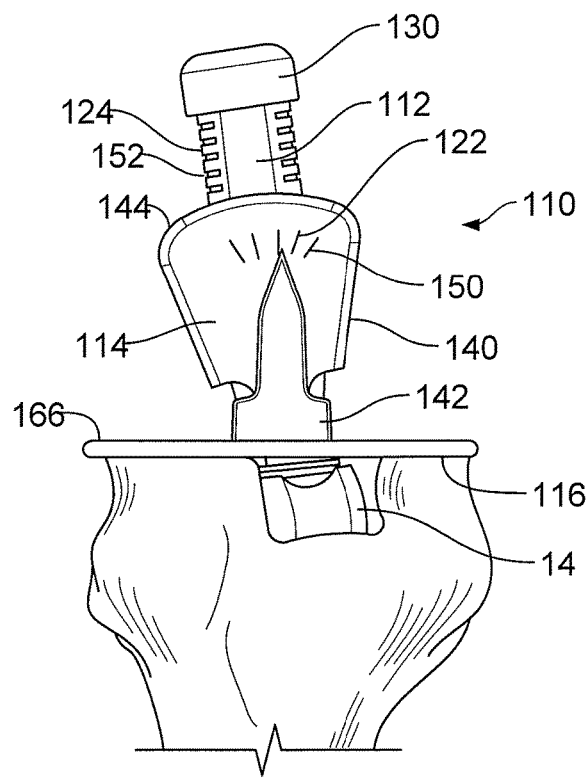
FIG. 14A is a side view of an anatomic guide coupled to the stem in the bone.
Figure 14B:
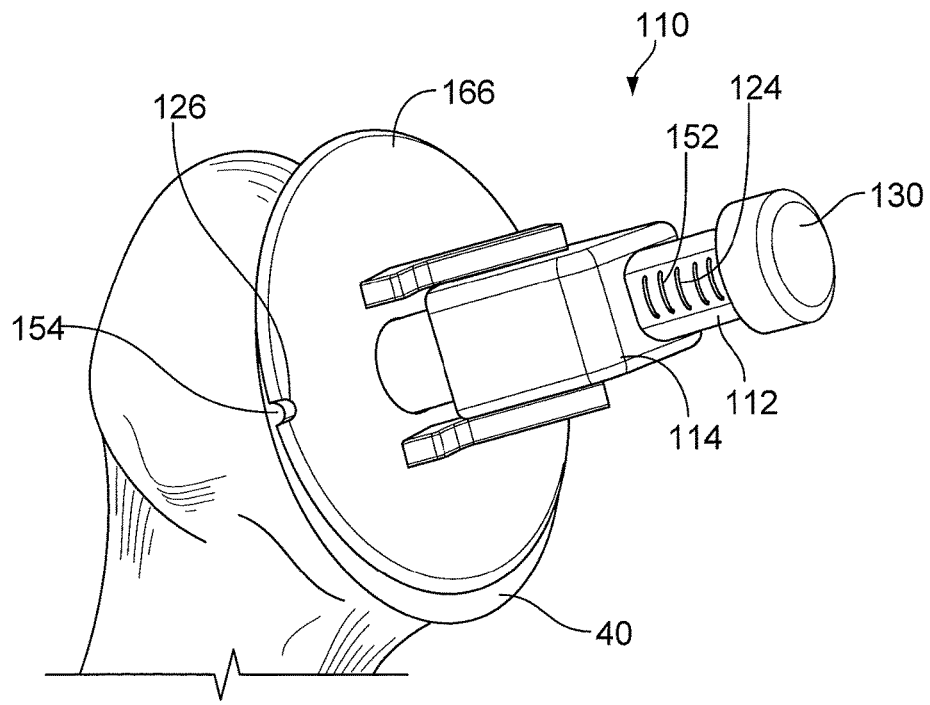
FIG. 14B is a perspective view of FIG. 14A.

Referring to FIGS. 14A and 14B, an anatomic guide 110 includes a first member 112 and a second member 114 coupled to the first member 112 such that the second member 114 can slide and tilt relative to the first member 112. The second member 114 includes a surface 116 for contacting a bone osteotomy 40 such that with the surface 116 in contact with the bone osteotomy 40, the relative sliding and tilt of the second member 114 relative to the first member 112 identifies an anatomic implant component 120 (FIG. 19A) for use with an implant stem 14. The guide 110 includes indicators 122, 124, and 126 that aid in identifying a desired anatomic implant component 120.

Figure 15:
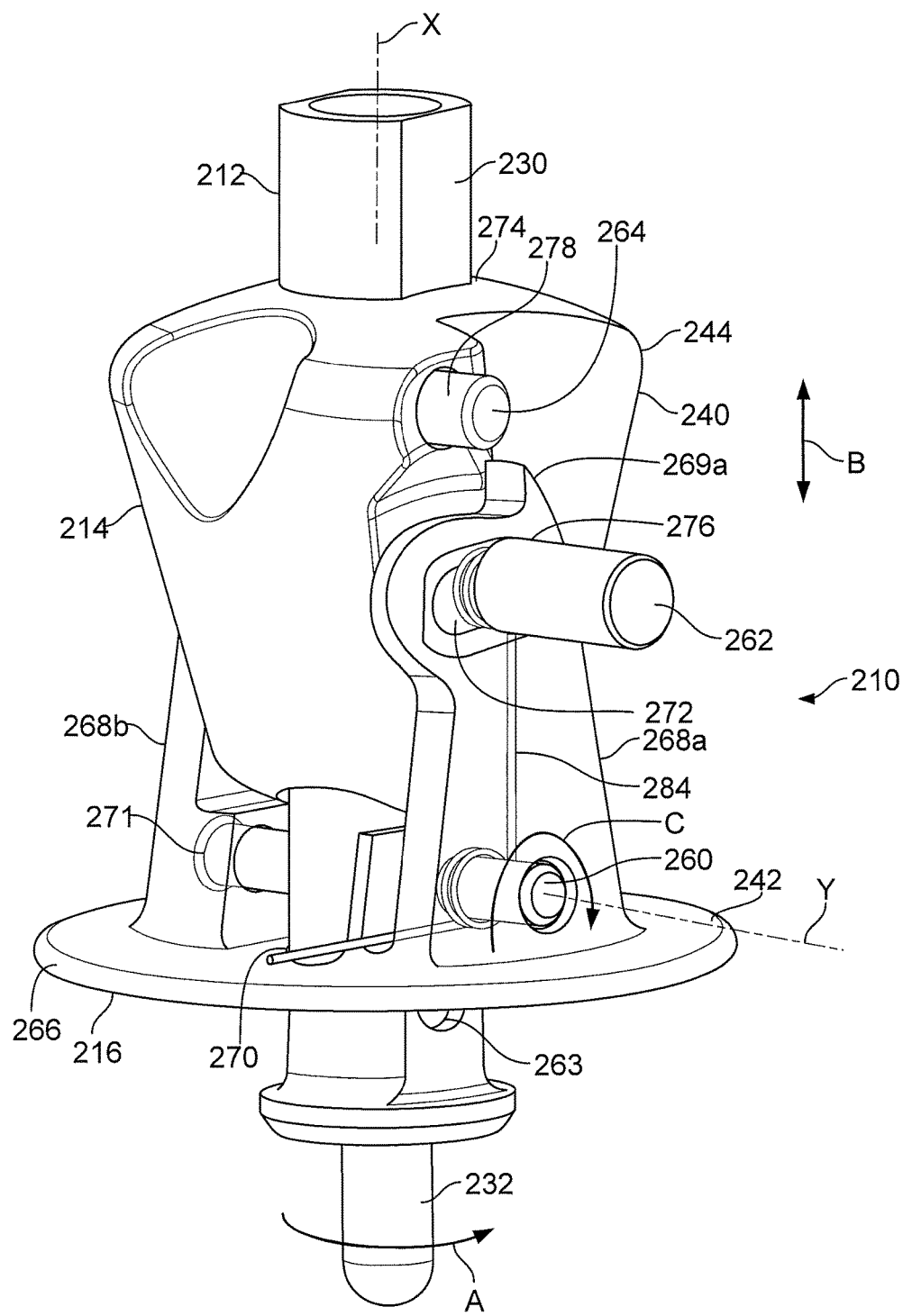
FIG. 15 is a perspective view of an alternative implementation of the anatomic guide of FIG. 14.

Referring to FIG. 15, in an alternative implementation of the anatomic guide 110, a first member 212 of an anatomic guide 210 includes a shaft 230 with a terminal nipple 232. In use, the terminal nipple 232 is received by the shoulder stem 14 (FIG. 14A) to align the guide 210 with the shoulder stem 14 and to allow rotation of the guide 210 relative to the shoulder stem (arrow A). A second member 214 is received over the shaft 230 to be slidable along the shaft (arrow B) and liftable relative to the shaft (arrow C). The unrestrained relative sliding and tilting of the second member 214 relative to the first member 212 positioned in alignment with the stem 14 makes it possible to provide measurement of the angle of the inclination-version combination. The second member 214 includes a handle gage 240 having a first portion 242 and a second portion 244. The portions 242, 244 slide together relative to the shaft 230, and the first portion 242 is tiltable relative to the second portion 244 and the shaft 230.

Referring again to FIGS. 14A and 14B, the indicator 122 includes indicia 150 on both sides of a second portion 144 of a handle gage 140 that identify the relative tilt of a first portion 142 of the handle gage 140, and the indicator 124 includes indicia 152 that identify the relative sliding of the handle gage 140. The indicator 126 includes a formation, for example, a cut-out 154, on the handle gage 140 that is used to indicate on the osteotomy the rotational alignment of the guide 110 relative to the osteotomy 40. The cut-out 154 is located in the same plane as the plane within which the first portion 142 tilts.

Figure 16B:
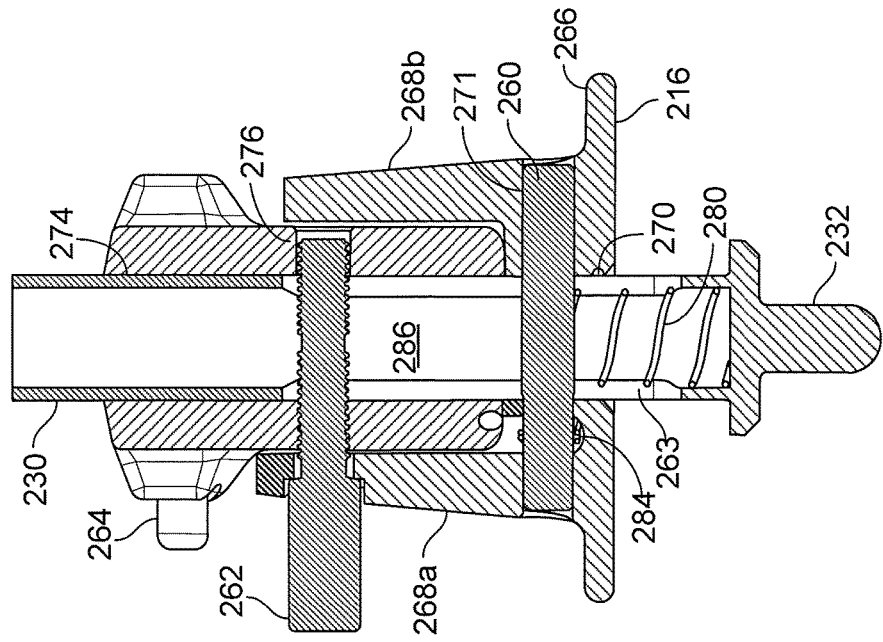
FIG. 16B is a cross-sectional view of the anatomic guide taken along lines 16B-16B, in FIG. 16A.
Figure 16A:
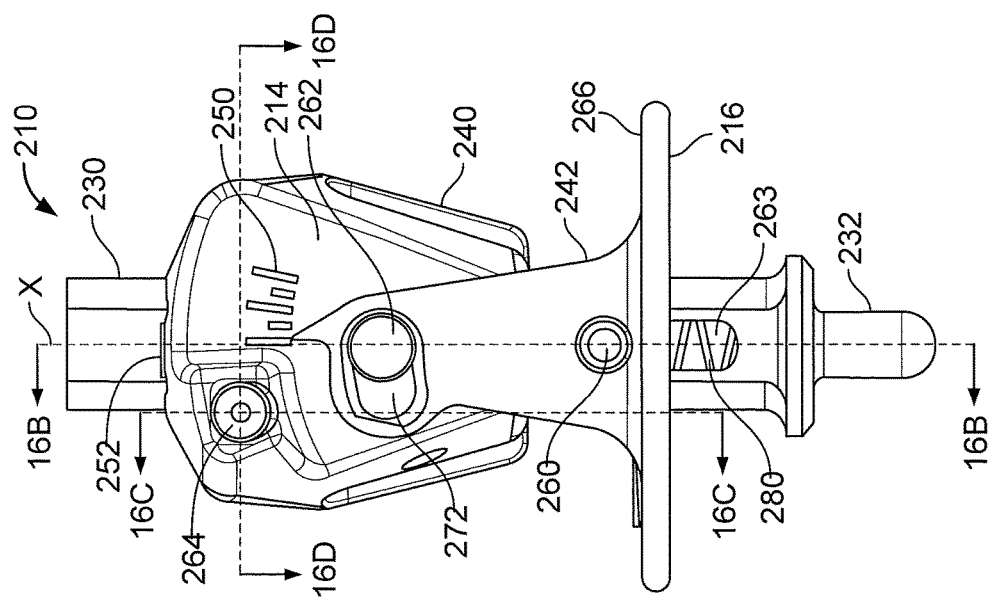
FIG. 16A is a side view of the anatomic guide of FIG. 15.

Referring again to FIG. 15, the handle gage 240 is coupled to the shaft 230 by a pin 260 and a thumb screw 262. The pin 260 and the thumb screw 262 are received within axial slots 263 in the shaft 230 such that the handle gage 240 can slide axially along a longitudinal axis, X, relative to the shaft 230. The first portion 242 of the handle gage 240 tilts relative to the second portion 244 about an axis, Y, of the pin 260, and indicia 250 (FIG. 16A) indicate the relative tilt. The shaft 230 and the handle gage 240 rotate together about the axis, X, due to the non-circular shape formed by engaging flat surfaces 265 (FIG. 16D) of the shaft 230, first portion 242, and second portion 244. The shaft 230 and the handle gage 240 are also coupled by a lock pin 264 that is used to lock the relative axial position of the shaft 230 and the handle gage 240.

The first portion 242 of the handle gage 240 includes a skirt 266 that defines a surface 216 in contact with the bone osteotomy 40, and a pair of arms 268a, 268b. The skirt 266 defines a through hole 270 for receiving the shaft 230, and the second portion 244 of the handle gage 240 is received between the arms 268a, 268b. The hole 270 provides clearance between the skirt 266 and the shaft 230 to permit the tilting motion of the skirt 266. The arms 268a, 268b terminate in pointers 269a, 269b (FIG. 18C) that point to the indicia 250 to indicate relative tilt. Each arm 268a, 268b defines a through hole 271 for receiving the pin 260, and the arm 268a defines a second, slotted through hole 272 for receiving thumb screw 262. The slotted through hole 272 provides clearance with the thumb screw 262 to permit the tilting motion. The second portion 244 of the handle gage 240 defines a lumen 274 for receiving the shaft 230, and a pair of opposed through holes 276 for receiving the thumb screw 262.

The pin 260 and the thumb screw 262 are centrally aligned along the axis, X. However, the lock pin 264 is positioned off axis such that the lock pin 264 engages with an outer surface of the shaft 230, as described below. The second portion 244 of the handle gage defines a through bore 278 for receiving the lock pin 264.

Referring to FIGS. 16A-16E, the guide 210 includes three biasing springs 280, 282, and 284. The shaft 230 defines an axial lumen 286 (FIG. 16B) in which the spring 280 is located, between the nipple 232 and the pin 260. The spring 280 acts upon the pin 260 to bias the handle gage 240 in a direction away from the nipple 232. The axial slots 263 communicate with the lumen 286 to permit passage of the pin 260 and thumb screw 262 through the shaft 230. The spring 282 (FIG. 16C) is located in the lock pin through bore 278 and biases the lock pin 264 into engagement with the shaft 230. The spring 284 (FIGS. 15 and 16B) is a torsion spring that acts between pin 260 and the second portion 244 of the handle gage 240 to bias first portion 242 toward a neutral tilt position.

Figure 16C:
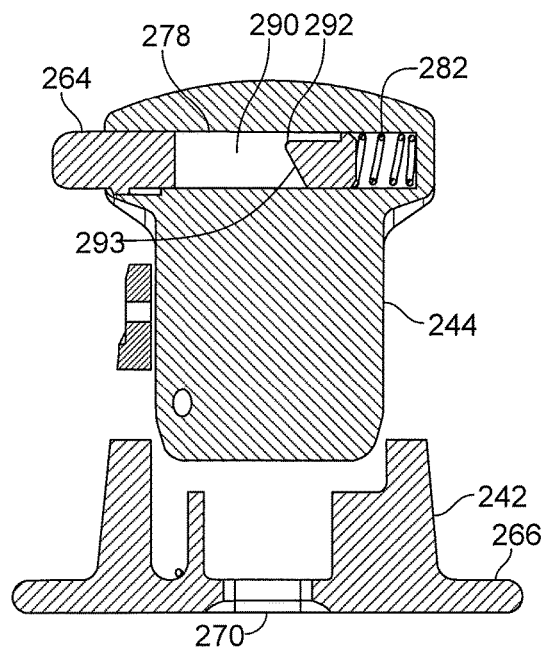
FIG. 16C is a cross-sectional view of the anatomic guide taken along lines 16C-16C, in FIG. 16A.
Figure 16D:
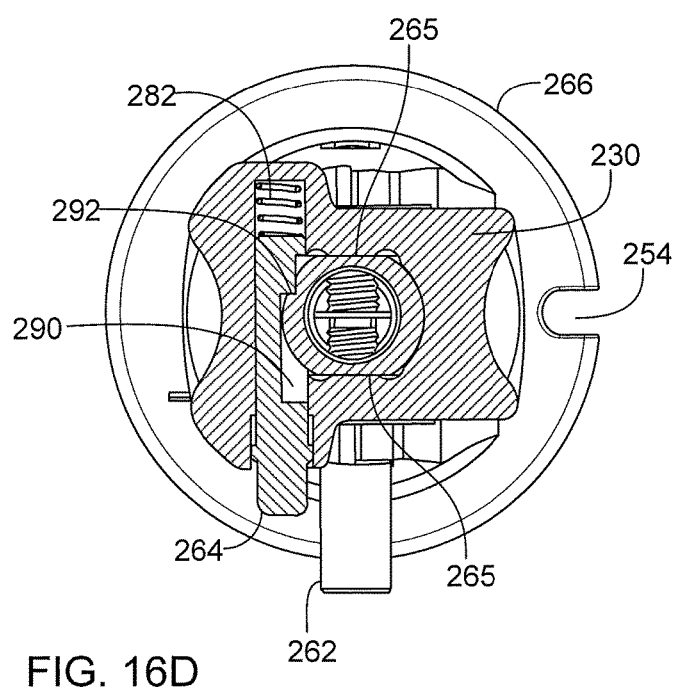
FIG. 16D is a cross-sectional view of the anatomic guide taken along lines 16D-16D, in FIG. 16A.
Figure 16E:
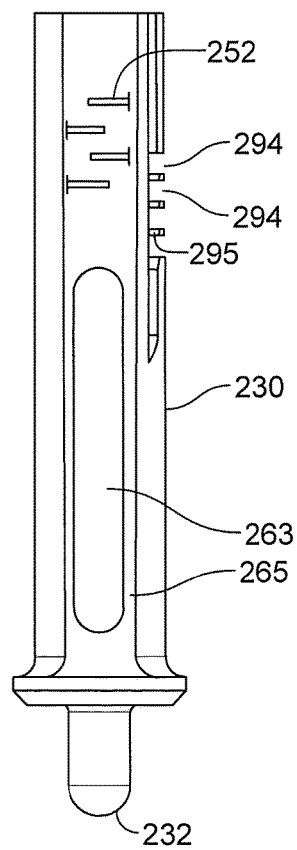
FIG. 16E is a side view of a shaft of the anatomic guide of FIG. 15.

Referring particularly to FIGS. 16C-16E, the lock pin 264 defines a groove 290 forming a shelf 292. The shelf 292 engages in detents 294 formed on the surface of the shaft 230. To slide the handle gage 240 relative to the shaft 230, the user pushes on the first portion 244 of handle gage 240. In doing so, engagement between a cam face 293 of the lock pin shelf 292 and a mating cam face 295 of the shaft 230 forces the lock pin 264 further against the spring 282, thereby disengaging the shelf 292 from the detent 294. When the user reaches a certain axial position along the shaft 230, the spring 282 forces the shelf 292 of the lock pin 264 into engagement with the next detent 294. Indicia 252 indicate the relative axial location of the handle gage 240. To return the guide 210 to a neutral axial position, the user depresses the lock pin 264, compressing the spring 282, allowing the spring 280 to return the shaft 230 to a neutral position relative to the handle gage 240. Contact between the thumb screw 262 and the slot 263 of the shaft 230 serves as a hard stop.

Referring again to FIGS. 5A and 5B, during shoulder replacement surgery, the surgeon forms a bore in the bone to receive the implant stem 14, and forms the humeral osteotomy 40. The bore includes a channel 45 in which the implant stem 14 sits. The implant stem 14 defines a hole 46 in which the nipple 32 can be placed. As can be seen in FIG. 5B, the implant stem 14 is typically not oriented parallel with the osteotomy 40. To select an implant component that will provide a known orientation of the implant relative to the osteotomy 40, for example, a parallel orientation, the surgeon uses the guide 210.

Figure 17A:
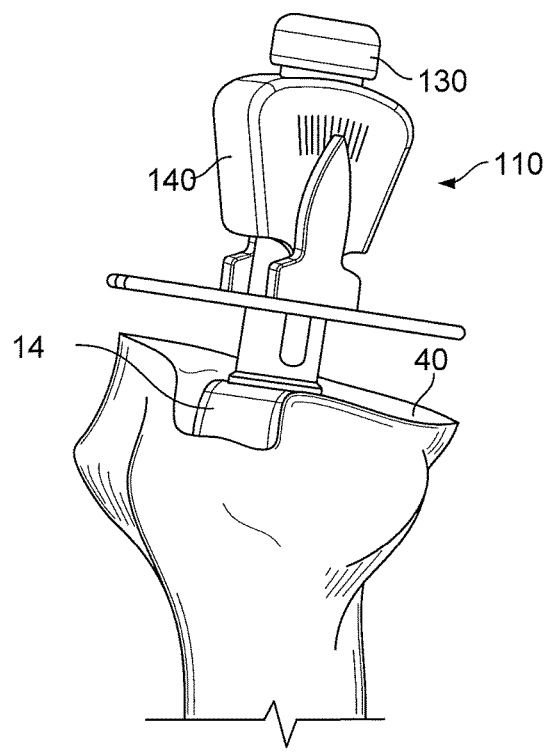
FIGS. 17A and 17B illustrate the guide of FIG. 14 in use.
Figure 17B:
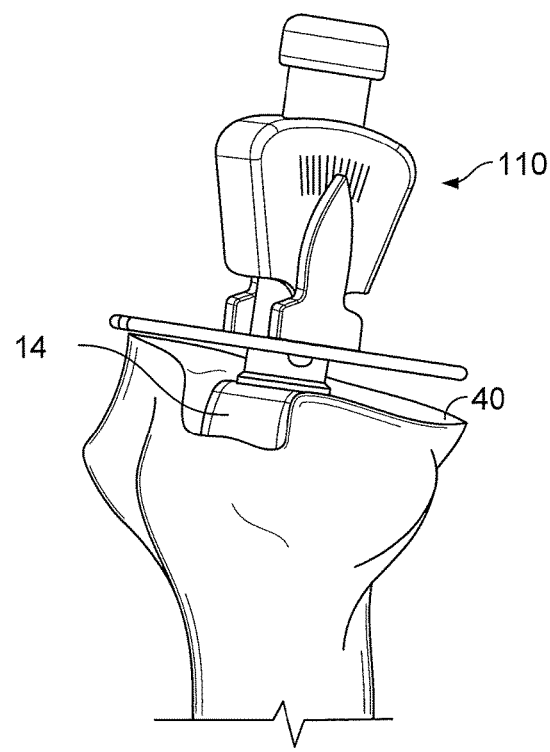

Referring now to FIGS. 17 and 14, in use, the surgeon seats a guide nipple (not shown) in the stem hole 46 and slides the handle gage 140 down the shaft 130 toward the osteotomy 40. By rotating the guide 110 relative to the stem 14 and tilting the handle gage 140, the surgeon finds the orientation of the guide at which the surface 116 of the skirt 166 lies flush with the osteotomy 40 (FIG. 14A).

Referring to FIGS. 18A-18E, in use, after creating the osteotomy 40 and the channel 45 for the stem 14 in the humerus 42 (FIG. 18A), the surgeon places the stem 14 in the channel 45. The compound angle guide 210 can then be used to determine the location of a mark 296 on the bone surface 44, as well as the desired angulation and length of, for example, the component 120 (FIG. 19). The surgeon manipulates the guide 210 (FIG. 18B) until an the skirt portion 266 of the guide 210 lies flush on the bone surface 44 (FIG. 18C). For example, by rotating the guide 210 relative to the stem 14 and tilting the handle gage 240 about the axis, Y, of the pin 260, the surgeon finds the orientation of the guide at which the surface 216 of the skirt 266 lies flush with the osteotomy 40. The surgeon then turns the thumb screw 262 to lock the relative tilt of the second portion 244 of the handle gage 240, and marks a spot 296 (FIG. 18D) on the osteotomy corresponding to cutout 254 to indicate the rotational alignment. The lock pin 264 automatically locks the relative axial position of the handle gage 240. As illustrated in FIG. 18E, indicia 250, 252 on the guide 210 indicate the desired angulation and length, respectively, the component 120.

The surgeon then removes the guide 210 from the stem 14 and selects an implant component 120 that corresponds to the indicated tilt and height (axial position) to produce the desired component orientation (FIGS. 19A and 19B). When implanted, a notch or mark 298 on the implant is aligned with the marked spot 296. The tilt indicia and the marked spot 296 account for the off-parallel orientation of the channel 45 relative to the osteotomy face 40, and the height indicia accounts for the fact that the depth of the channel 45 that the surgeon forms, and therefore how far the stem 14 is recessed within the bone, can vary between patients.

Figure 20A:
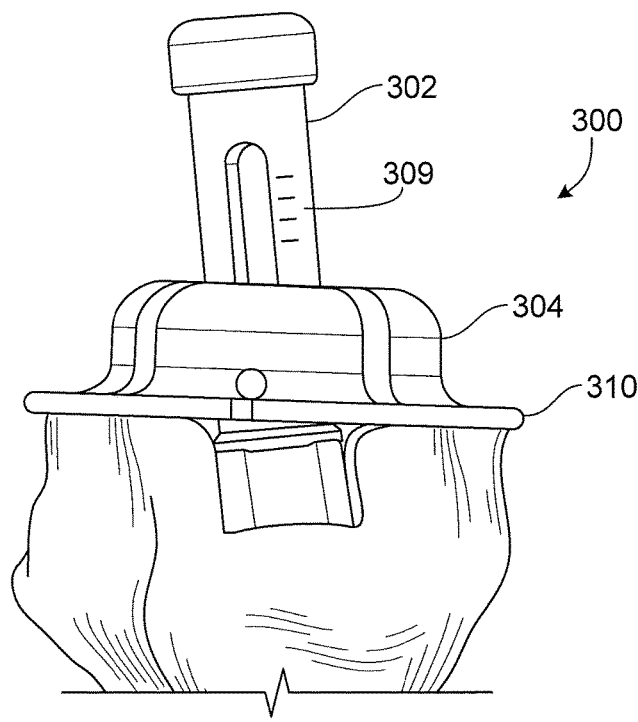
FIGS. 20A-20C illustrate another alternative implementation of an anatomic guide.
Figure 20B:
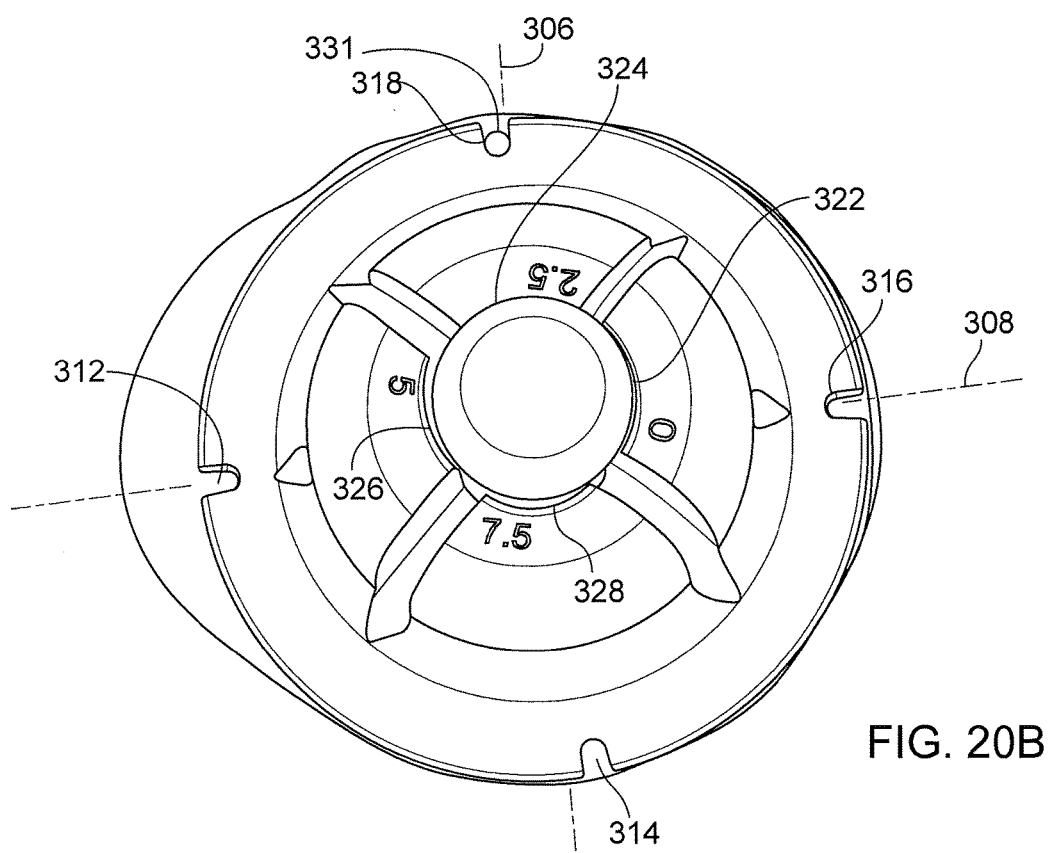

Referring to FIGS. 20A and 20B, in an alternative implementation, a guide 300 includes a first member, for example, a shaft 302, and a second member, for example, a handle gage 304 formed from a unitary portion, that slides axially and tilts relative to the shaft 302. In contrast to guide 110, 210 described above, rather than providing continuous adjustability along a single tilt plane, the handle gage 304 of guide 300 can be set at a number of discrete tilt angles by tilting along a number of discrete planes. In the illustrated implementation, the handle gage 304 can be set at four angles (0°, 2.5°, 5°, and 7.5°) by tilting along two discrete planes, 306, 308.

The shaft 302 includes indicia 309 for indicating the relative sliding of the handle gage 304, and a skirt 310 of the handle gage 304 includes formations, for example, cutouts 312, 314, 316, and 318 for indicating on the osteotomy 40 the relative rotation of the guide 300.

Figure 20C:
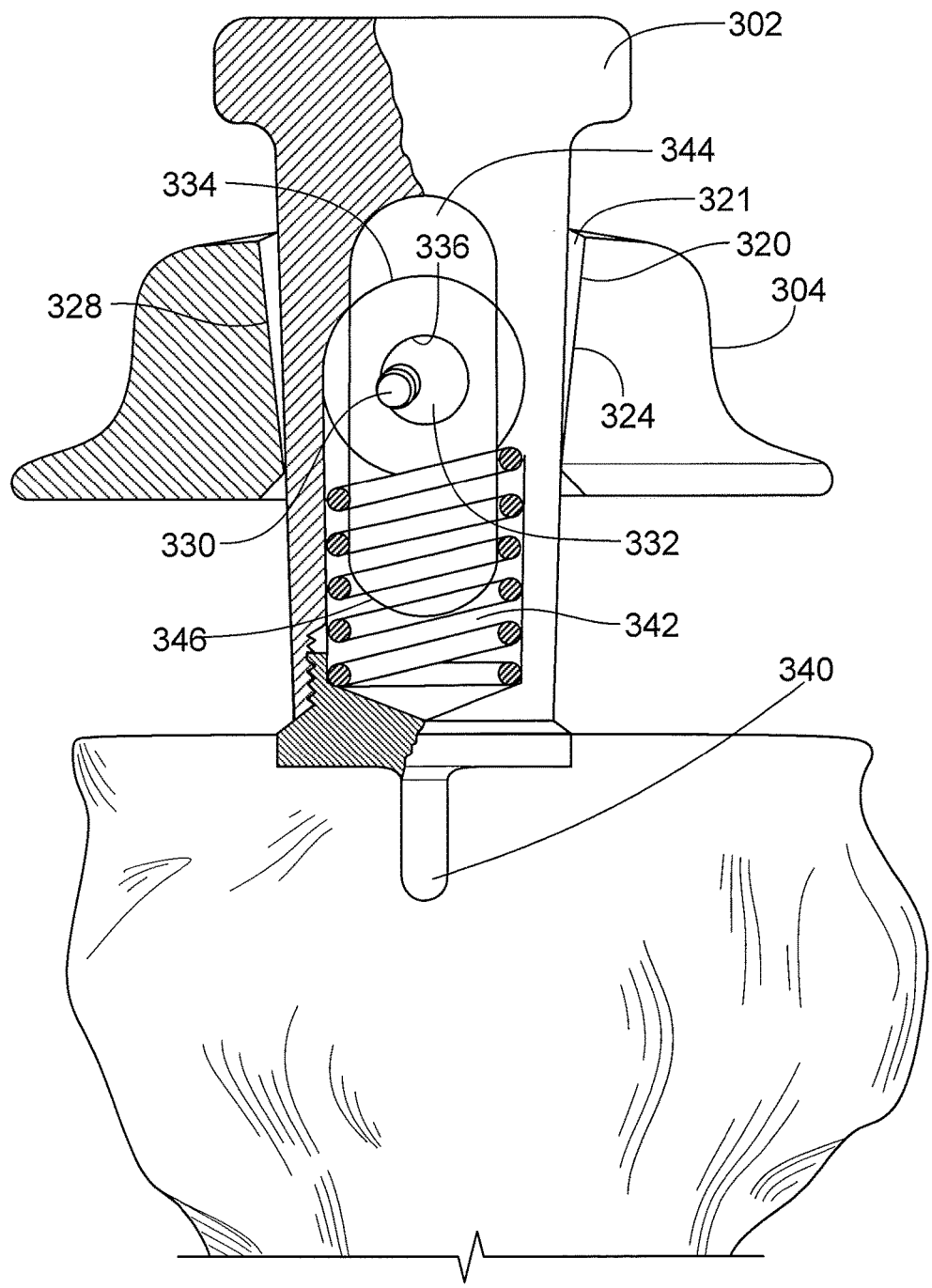

Referring also to FIG. 20C, the handle gage 304 has a wall 320 defining a lumen 321 that receives the shaft 302. The wall 320 has four quadrants 322, 324, 326, and 328, each set at a different angle with respect to the shaft 302. The handle 304 and shaft 302 are coupled by a pin 330 located within a cannulation 332 of a spherical ball 334. The shaft 302 defines a lumen 344 for receiving the ball 334, and slots 346 for receiving the pin 330. The clearance between the pin 330 and a wall 336 of the spherical ball 334 defining the cannulation 332 allows for the relative tilting of the handle gage 304 along planes 306, 308.

The shaft 302 includes a terminal nipple 340 for receipt within the stem 14, and a spring 342 located within shaft lumen 344 between the nipple 340 and the ball 334 to bias the handle gage 304 in a direction away from the nipple 340.

In use, the surgeon places the guide 300 on the implanted stem, picks one of the four tilt angles, and tilts the handle gage 304 relative to the shaft 302 to place the handle gage 304 at the selected angle. While holding the handle gage 304 at the selected angle, the surgeon advances the handle gage 304 toward the osteotomy 40 and rotates the guide 300 to determine how flat the skirt 310 sits on the osteotomy surface 44. The surgeon can repeat this process for all four angles to determine the best orientation of the handle gage 304.

The surgeon then marks the rotation orientation on the osteotomy 40 using the cutout located opposite the angled surface, e.g., if a 7.5° tilt provides the best fit, the surgeon would use cutout 318 to mark the rotational orientation, for example as marking 331. The surgeon then notes the axial indicia 309 for selecting the implant height, and the tilt angle for selecting the implant angle.

Figure 21:
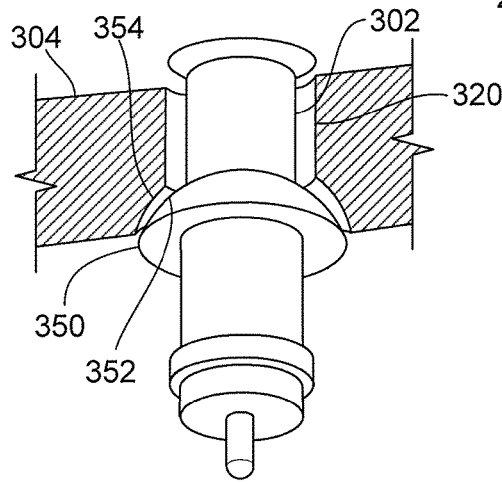
FIG. 21 illustrates another alternative implementation of an anatomic guide.

Referring to FIG. 21, to aid in indicating the relative sliding of the handle gage 304, the guide 300 can include a separate sliding component 350 that moves with the handle gage 304 relative to the shaft 302. When the handle gage 304 is released and moves upward under the force of the spring 342, the sliding component 350 remains in place relative to the indicia 309. The sliding component 350 has a spherical surface 352 that meets with a spherical chamfer 354 at the end of the handle gage wall 320 to facilitate the tilting of the handle gage 304.

Figure 22A:
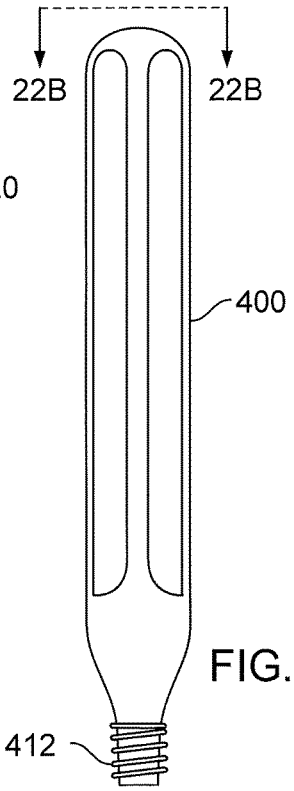
FIGS. 22A-23B illustrate another alternative implementation of an anatomic guide.
Figure 22B:
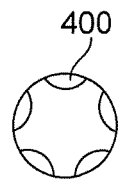
Figure 23A:
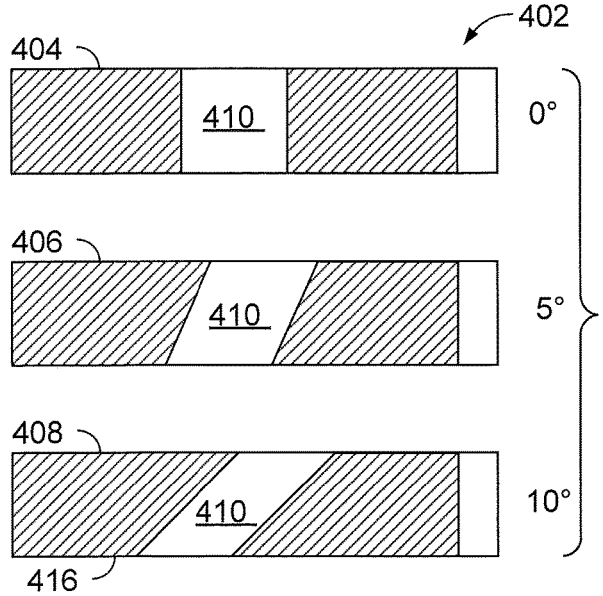
Figure 23B:
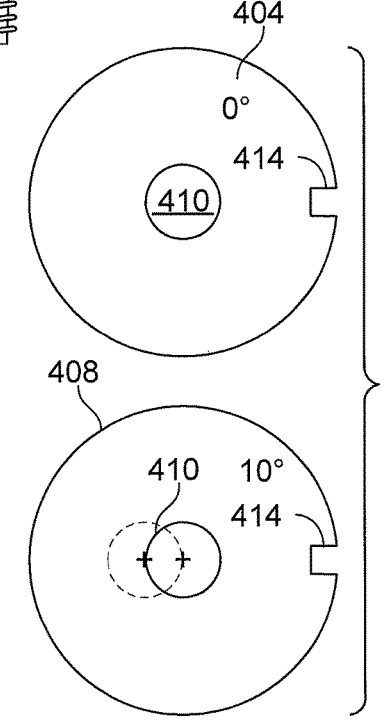

An additional alternative implementation of a guide is shown in FIGS. 22 and 23, which includes a shaft 400 a series of handle gages 402. In the illustrated implementation, three handle gages 404, 406, and 408 are shown, though more or fewer handles gages 402 can be used with shaft 400. Each handle gage 402 includes a bore 410 oriented at an angle, for example, 0°, 5°, and 10°. The shaft 400 has a threaded end 412 for threadedly engaging the stem 14. Each of the handle gages 402 includes a cut-out 414 for marking the rotational alignment of the handle gage 402 on the osteotomy.

In use, the surgeon attaches the shaft 400 to the stem 14, and selects one of the handles gages 402. The surgeon slides the handle gage 402 down the shaft 400, with the handle gage 402 oriented relative to the shaft 400 at the angle of the bore 410, and rotates the handle gage 402 relative to the shaft 400 to try to align the surface 416 of the handle gage 402 with the osteotomy 40. The surgeon can repeat this process with each handle gage 402 to determine the angle that provides the best alignment.

Referring to FIG. 25B and FIGS. 6A-6C, to aid the surgeon in setting the angulation of the connector 10, the first member 20 is provided with an indicia 560. By aligning the indicia 560 with indicia on an alignment member 586 (described below), which in turn is aligned with a mark 564 (FIG. 25D) on the bone surface 44, the first member 20 is set at the desired angulation; the mark 564 having previously been determined by the surgeon to correspond to the alignment point that produces the desired inclination and retroversion, as described above. In use, to align vector 50 and axis, Z, after the first member 20 is fixed to the stem 14, the second member 22 is coupled to the first member 20 and rotated until the vector 50 and axis, Z, align.

Figure 24A:
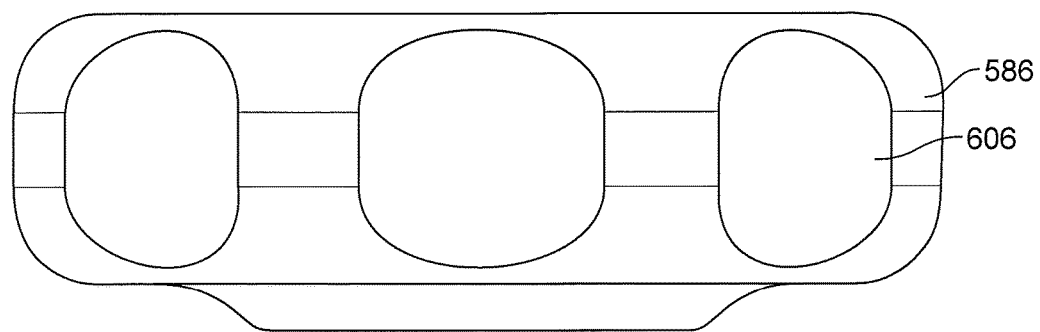
FIGS. 24A and 24B are side and cross-sectional views of an alternative implementation of an alignment member for use with the connector.
Figure 24B:
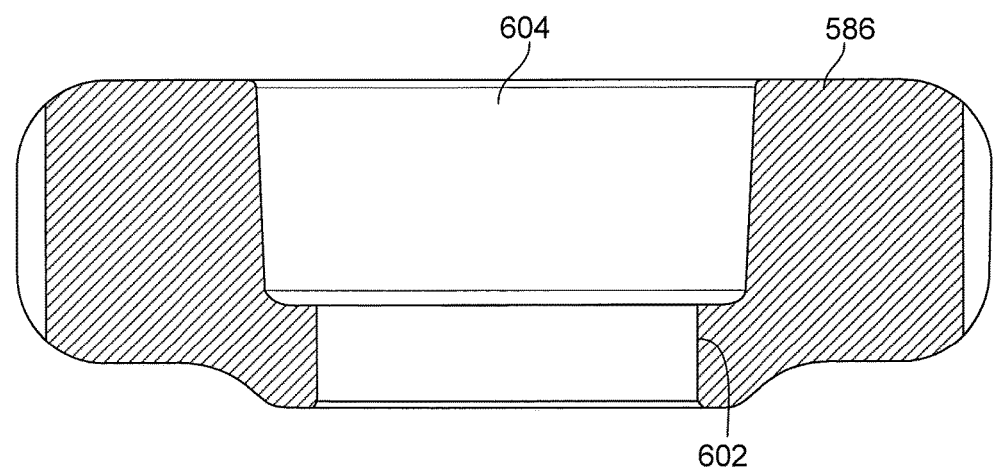

The surgeon uses an alignment member 586, illustrated in FIGS. 24A and 24B, to rotate the first and second members 20, 22 about the screw axis, X. The alignment member 586 defines a first bore 602 sized to receive the first member 20 in frictional engagement, and defines a second, larger bore 604 sized to receive the second member 22 in frictional engagement. The alignment member 586 outer circumference 606 is knurled to facilitate hand turning of the alignment member and frictionally engaged member.

Figure 25A:
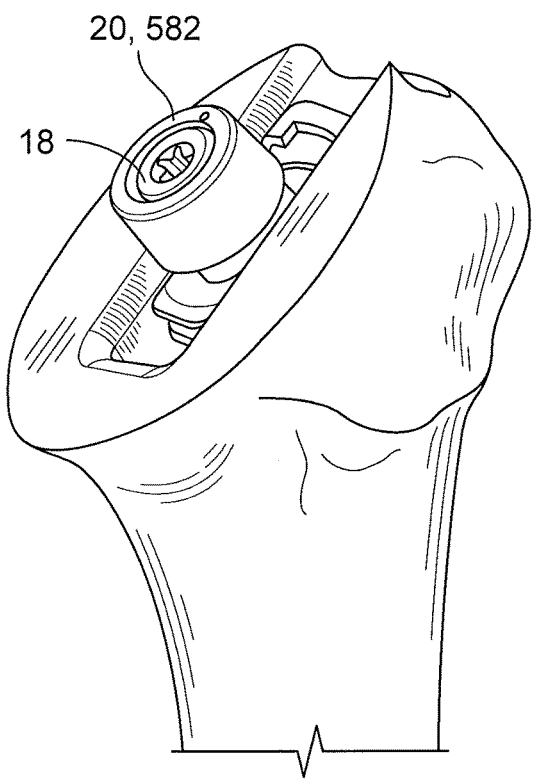
FIGS. 25A-25G illustrate the use of a trial connector and the alignment member of FIG. 24.
Figure 25B:
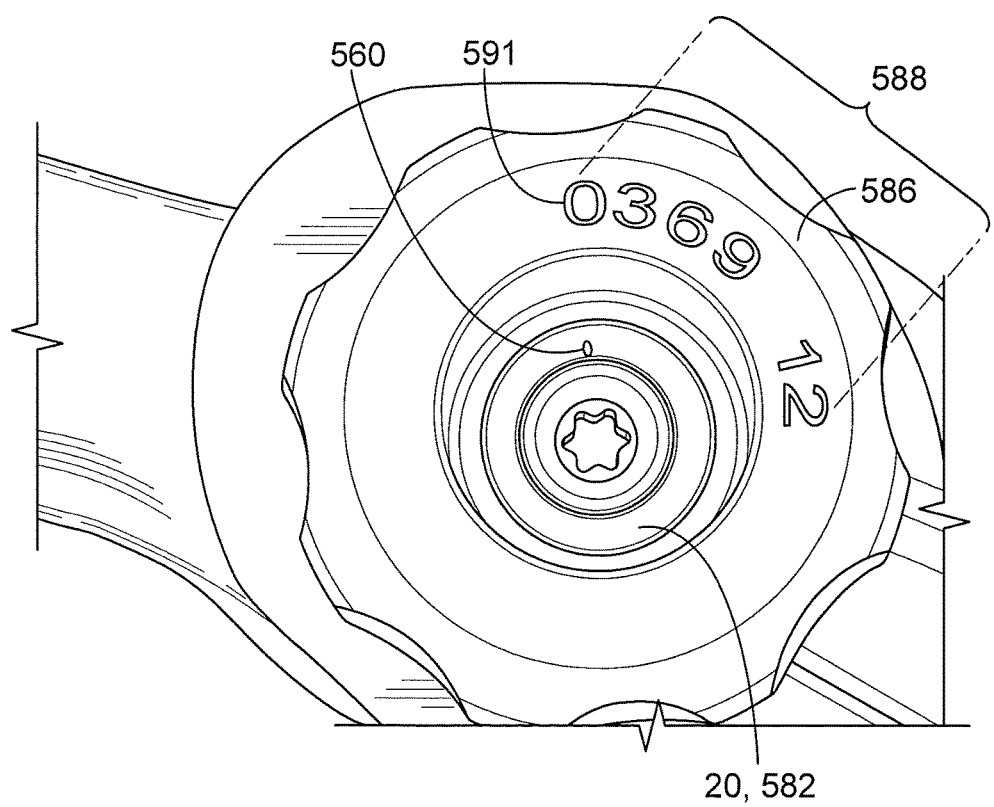
Figure 25C:
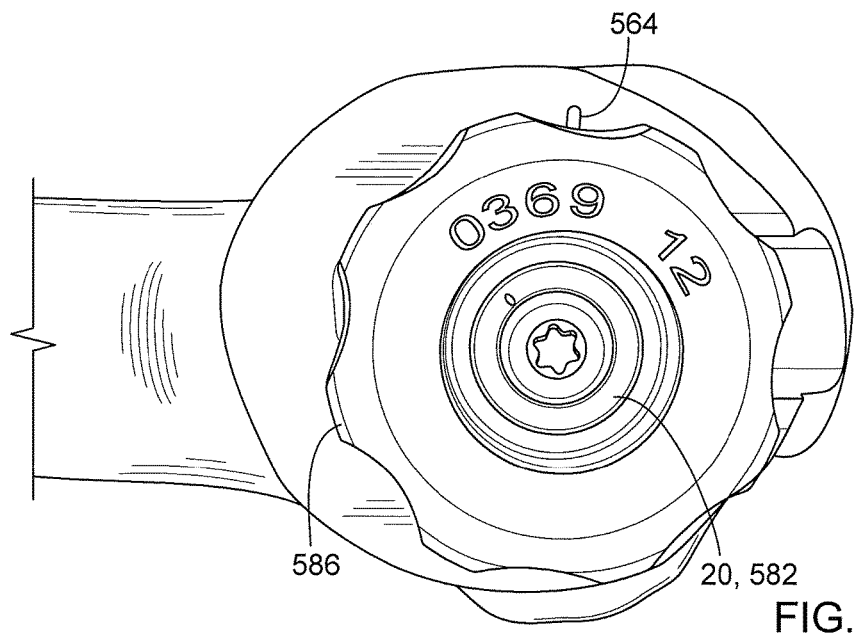
Figure 25D:
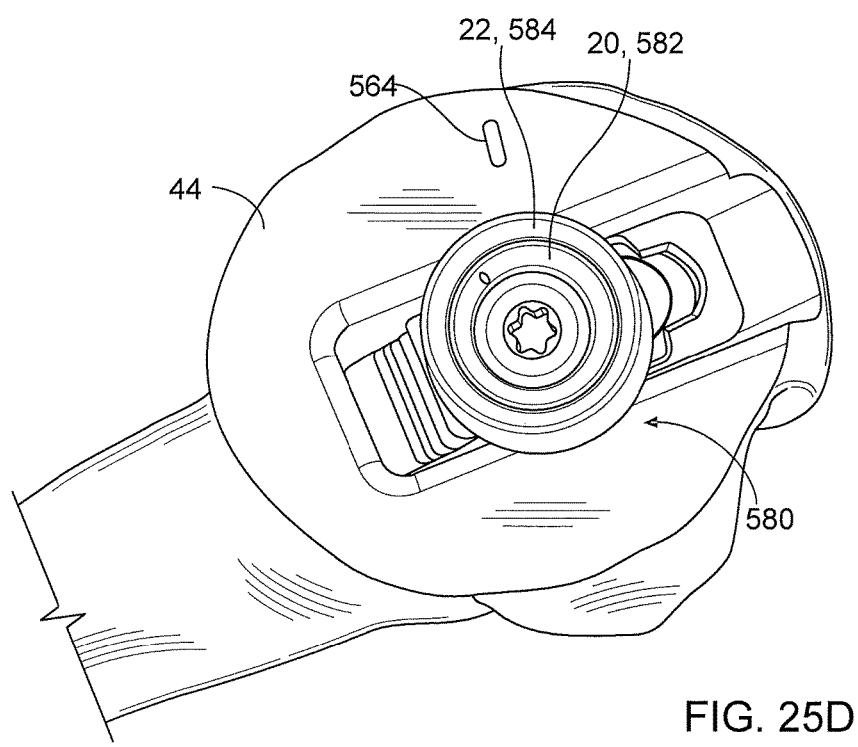

Referring to FIGS. 25A-25D, the surgeon then uses a trial connector 580 to check that the angulation, length, and alignment mark 564 produce the desired result. FIG. 25B shows indicia 560 on a first trial member 582 (corresponding to member 20) of the trial connector 580 aligned with a corresponding indicia 591 (the zero indicia) on the alignment member 586. To position the first trial member 582 as shown in FIG. 25B, after the surgeon couples the first trial member 582 to the stem 14 using the screw 18 (FIG. 25A), the surgeon slides the alignment member 586 over the first trial member 582 with indicia 560, 591 aligned. The surgeon then rotates the alignment member 586 and the first trial member 582 as a unit about the screw 518 to align angle indicia 588 (corresponding to the angulation indicated by the guide 110, 210, 300) with the mark 564 (FIG. 25C, here the angle is 8.5°). The surgeon then tightens the screw 18 to fix the position of the first trial member 582.

Figure 25E:
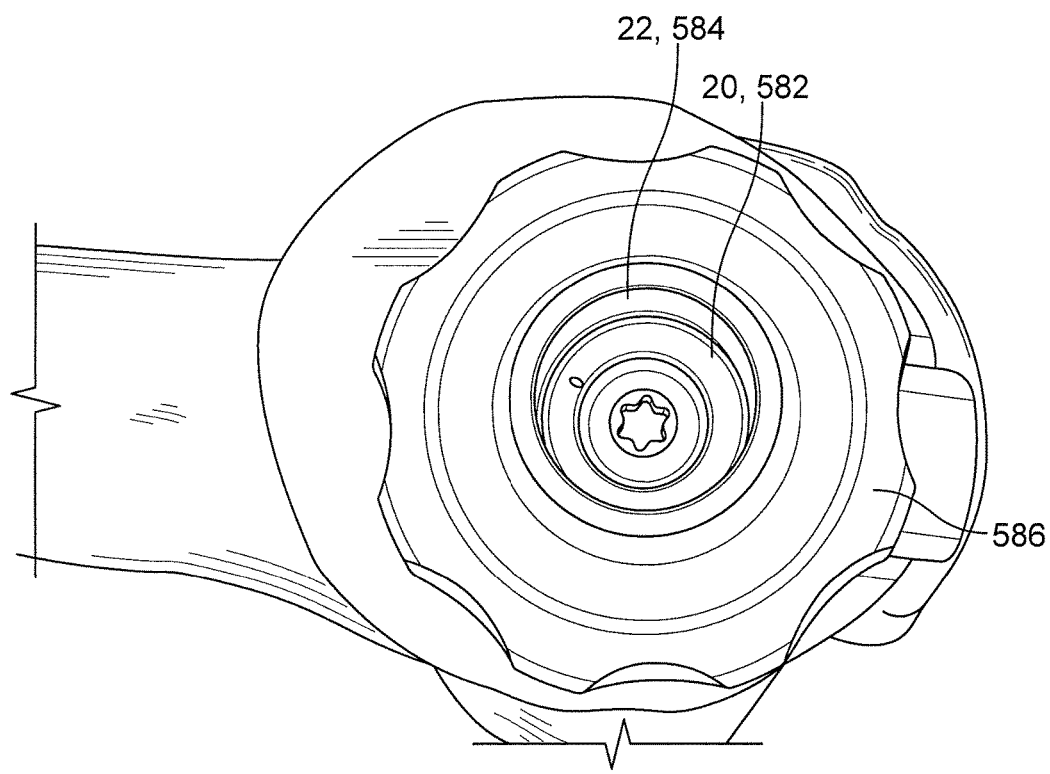
Figure 25F:
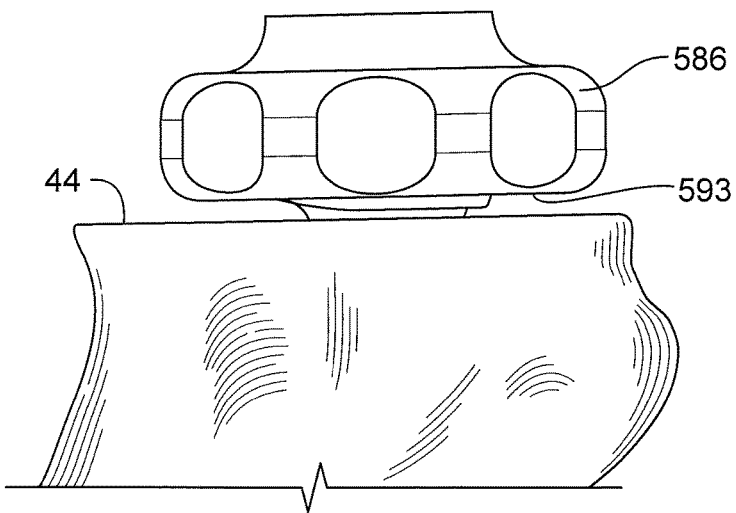
Figure 25G:
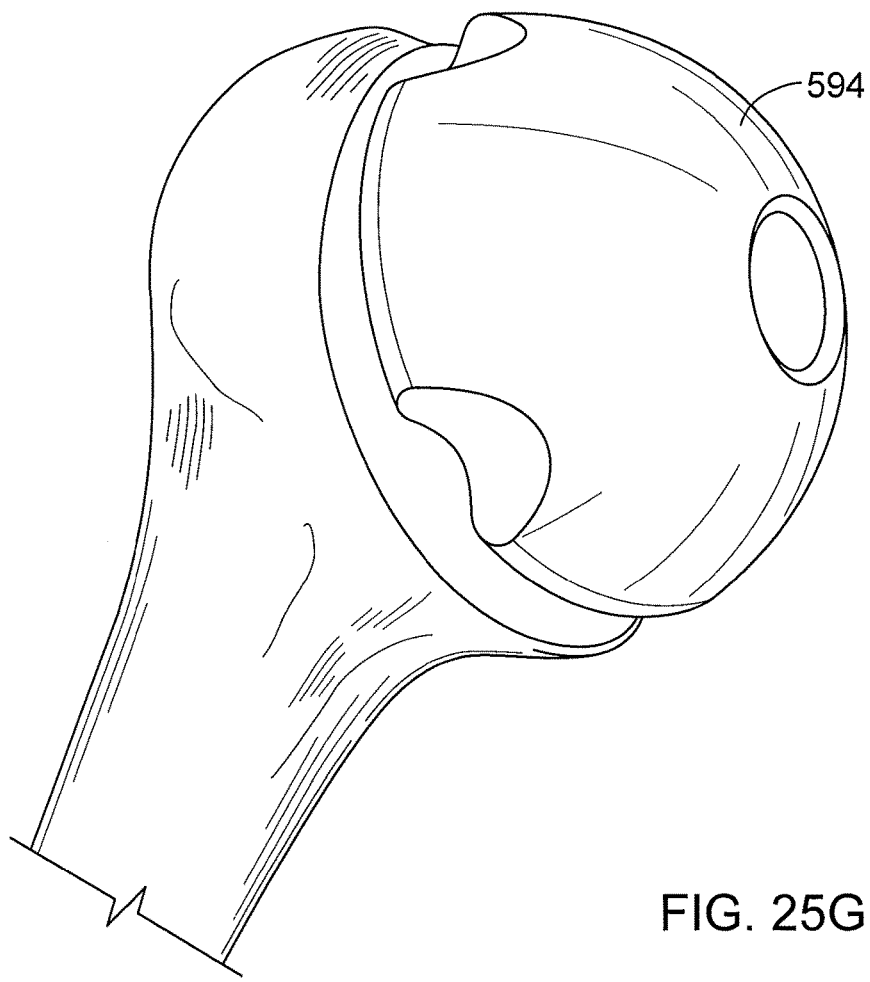

To place a second trial member 584 (corresponding to member 22) of the trial connector 580, the surgeon removes the alignment member 586 from the first trial member 582, slides the second trial member 584 (FIG. 25D) over the first trial member 582, flips over the alignment member 586 and slides the alignment member 586 over the second trial member 584 (FIG. 25E). The surgeon rotates the alignment member 586 and the second trial member 584 as a unit until a flat surface 593 of the alignment member is parallel with the bone surface 44. The second trial member 584 is selected to provide the desired length indicated by the guide 110, 210, 300. A trial head component 594 (FIG. 25G) is then coupled to the trial connector 580 and the head 594 is rotated to a position that provides optimal coverage of the bone surface 44. The surgeon then takes the implant through a trial range of motion.

Figures 26A, 26B, 26C:
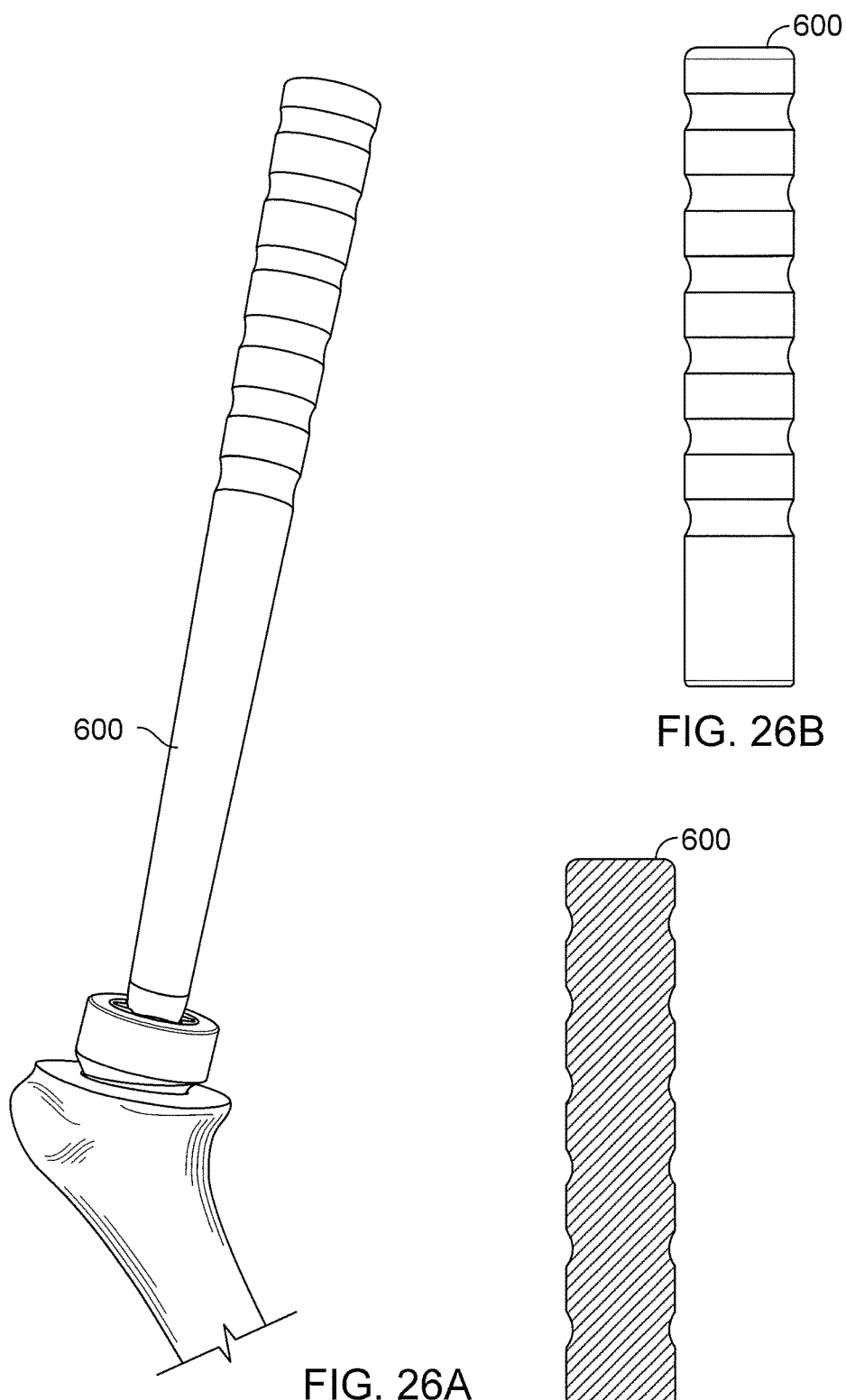
FIG. 26A illustrates the use of an impactor.
FIGS. 26B and 26C are side and cross-sectional views of the impactor.

If the trial connector 580 provides the desired functionality, the surgeon removes the trial connector 580, selects a member 20 having the desired length, and repeats the procedure described above for the trial connector to connect members 20, 22 to the stem 14. Once properly aligned (FIG. 25F), the surgeon uses an impactor 600 (FIGS. 26A-26C) to impact the member 22 such that the tapers 24, 26 (FIG. 2) fix the member 22 to the member 20, and removes the impactor 600 and alignment member 586. The surgeon then slides the head 12 over the member 22, rotates the head 12 to the position that provides optimal coverage of the bone surface 44, and impacts the head 12 such that the tapers 28, 30 (FIG. 2) fix the head 12 to the member 22.

Figure 27A:
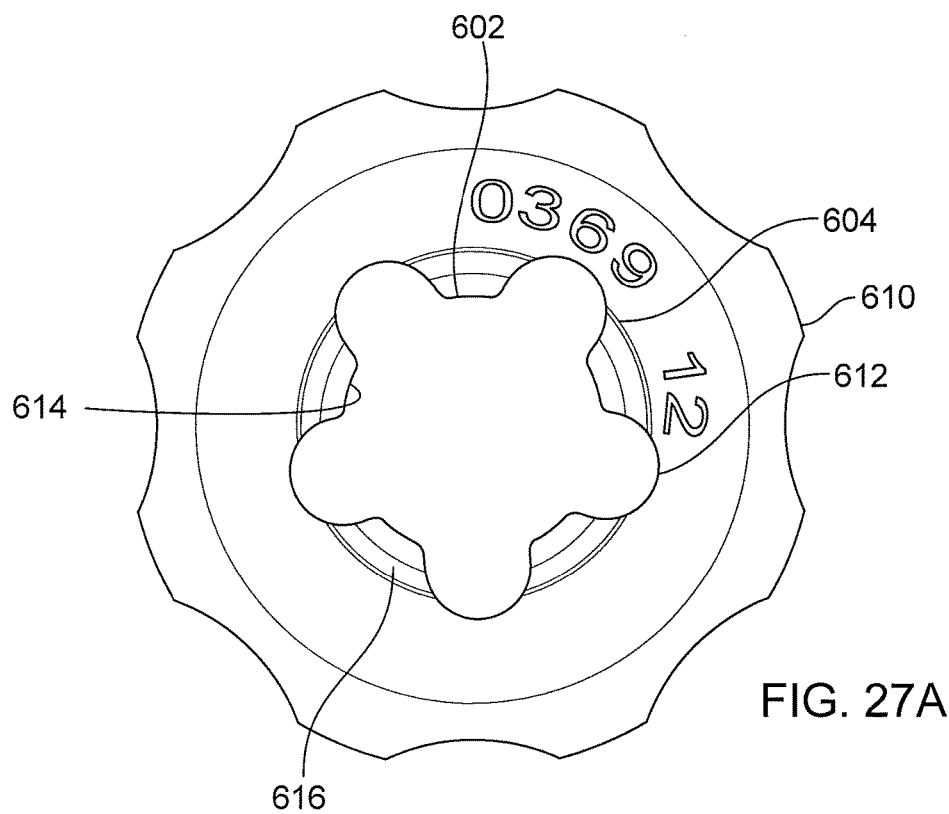
FIGS. 27A-27C are top, side, and cross-sectional views of another alternative implementation of an alignment member.
Figure 27B:
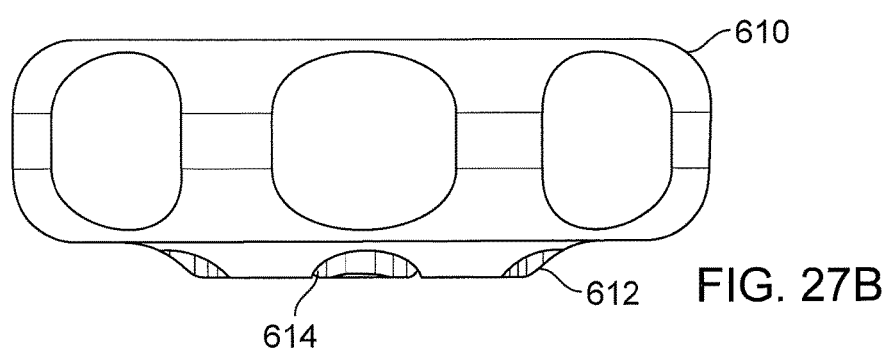
Figure 27C:
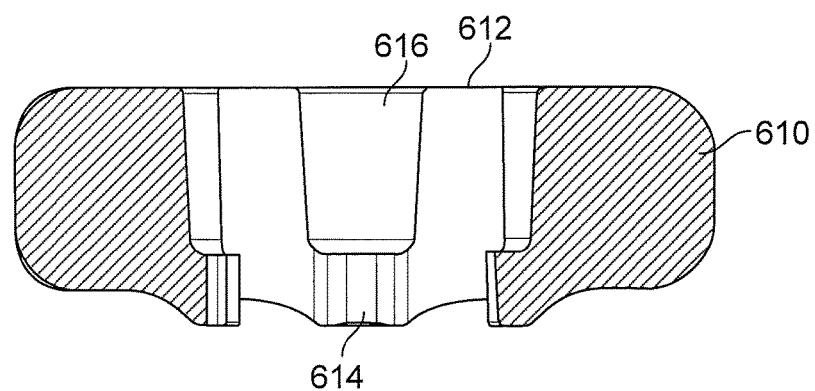
Figure 27D:
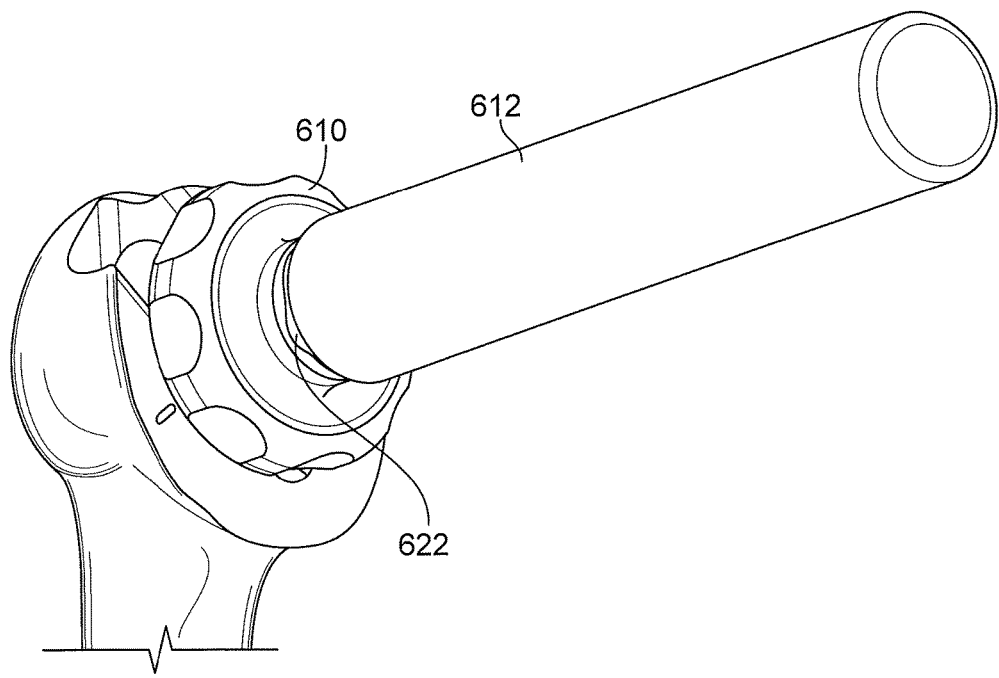
FIG. 27D illustrates the use of an alternative implementation of an impactor.
Figure 28:
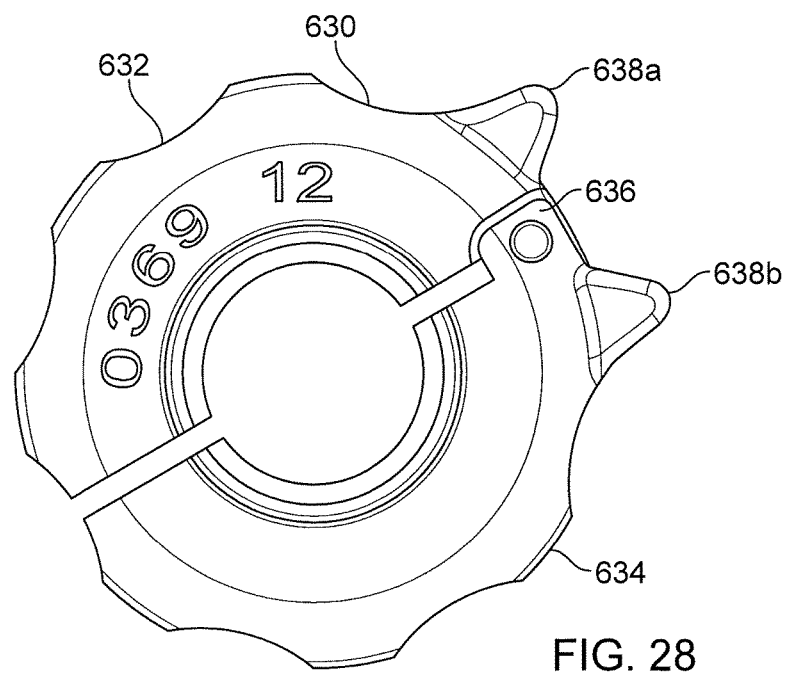
FIG. 28 is a top view of another alternative implementation of an alignment member.

Referring to FIGS. 27A-27C, in an alternative implementation, an alignment member 610 includes an internal petal pattern 612 that is cut through the wall 614 of the smaller bore 602 and into the wall 616 of the larger bore 604. The alignment member 610 is used with an impactor 620 (FIG. 27D) having a corresponding petal pattern 622 that is received within petal pattern 612. This allows the impactor 620 to directly contact the second member 22 such that the impaction force is applied directly to the second member 22 rather than through the alignment member, facilitating the ease of removal of the alignment member 610 from the second member 22. Alternatively, as illustrated in FIG. 28, an alignment member 630 includes two parts 632, 634 joined by a hinge 636. Each part 632, 634 includes a finger tab 638a, 638b that the surgeon presses toward each other to open the parts 632, 634 for removal from the second member 22. The parts 632, 634 can each define a petal pattern as illustrated in FIGS. 27A-27C.

Figure 29A:
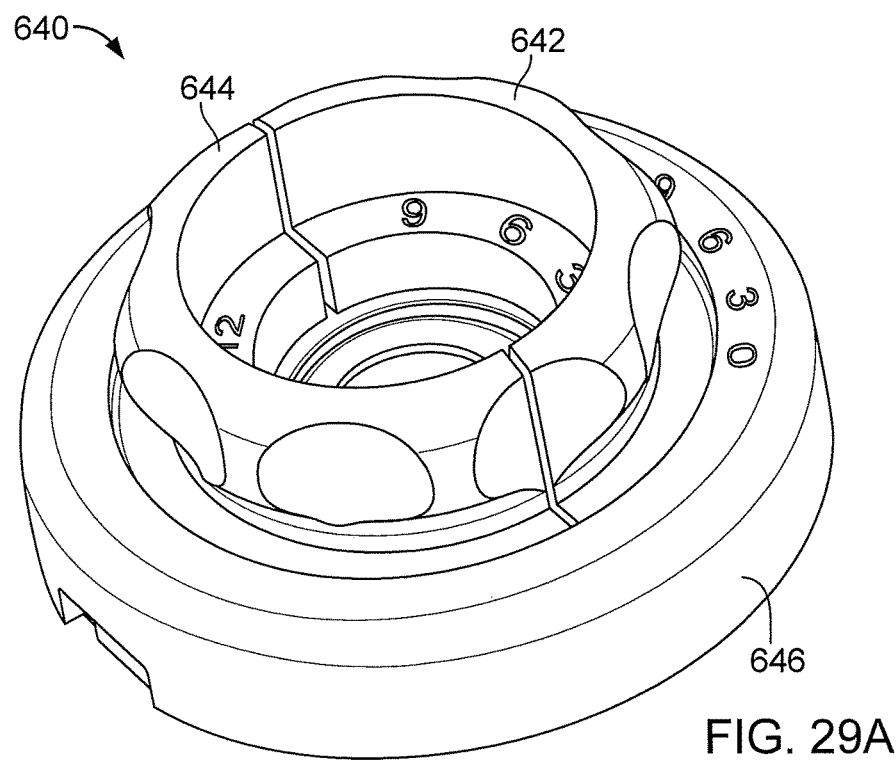
FIGS. 29A-29C illustrate a three-part alignment member.
Figure 29B:
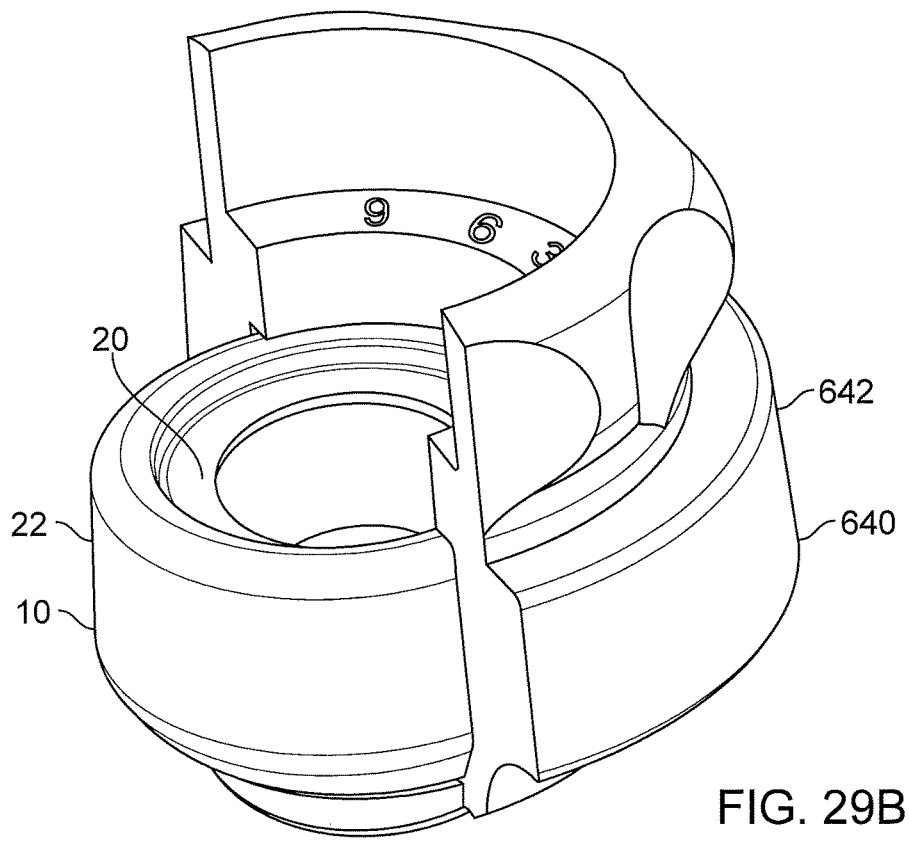
Figure 29C:
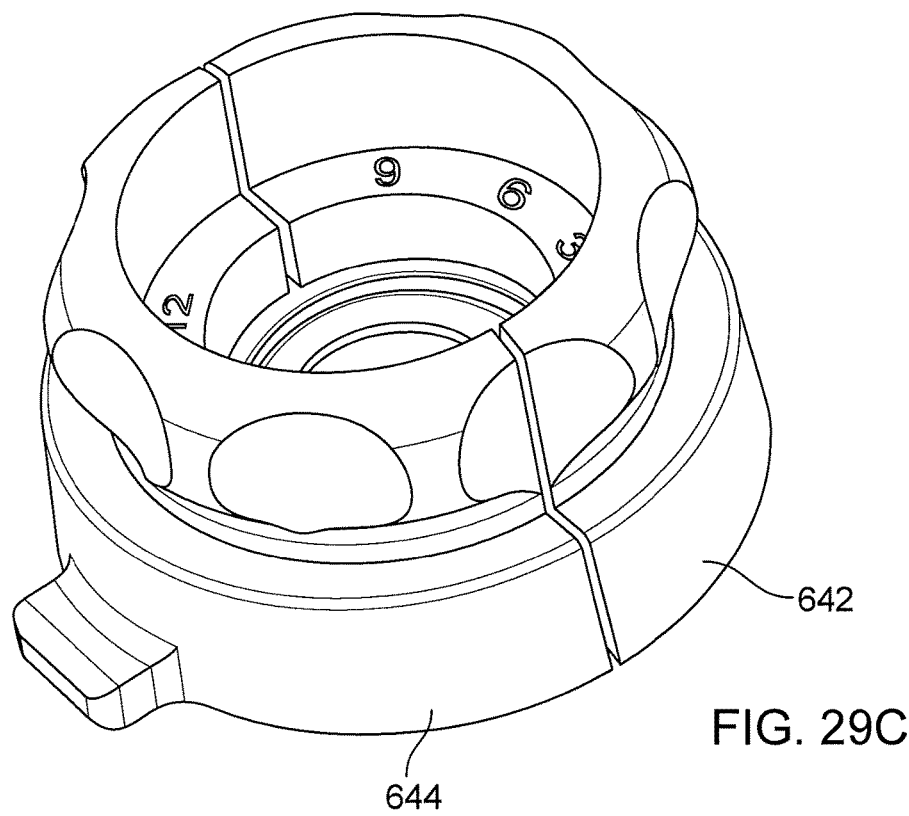

FIGS. 29A-29C illustrate a three part alignment member 640 having first and second parts 642, 644 that are secured together by an outer ring 646. To remove the alignment member 640 from the outer member 22, the surgeon slides off the outer ring 646 and separates the parts 642, 644.

Figure 31A:
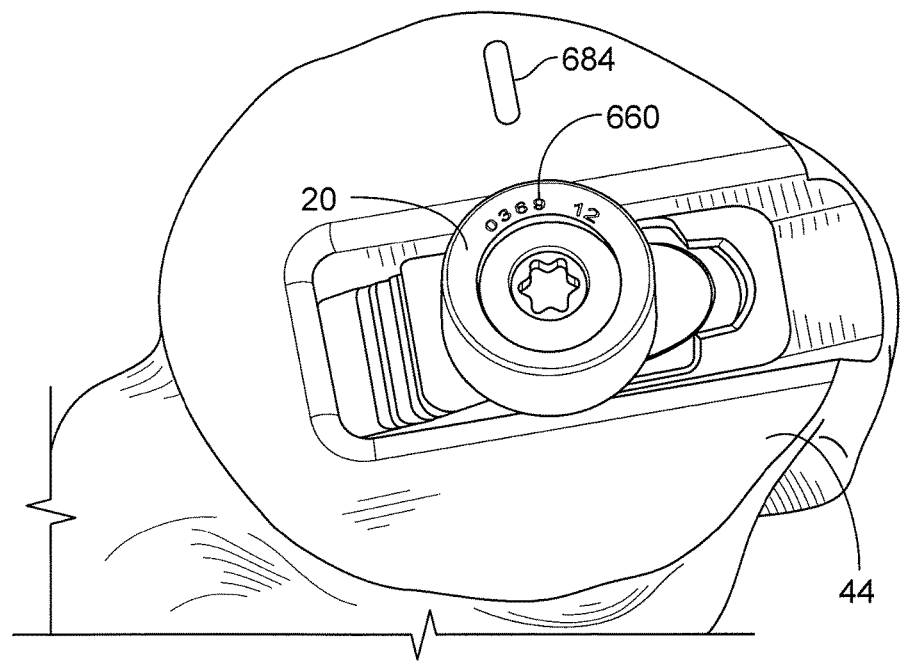
FIGS. 31A-31B illustrate an alignment of the connector.
Figure 31B:
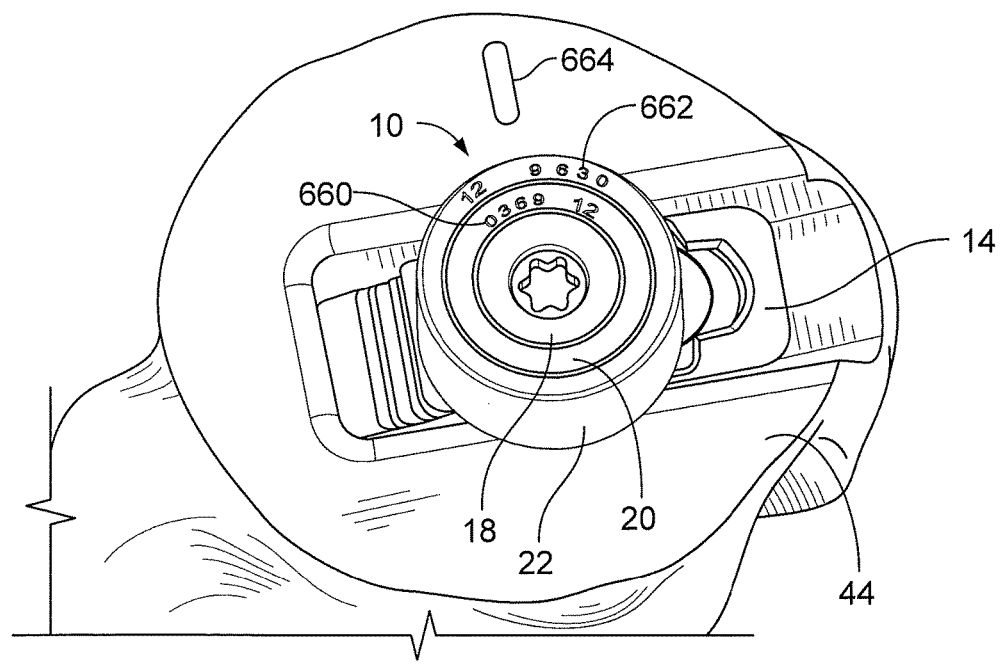

Referring to FIGS. 31A and 31B, to aid the surgeon in setting the angulation of the connector 10, the first member 20 is provided with angle indicia 660, for example, indicia representing 0-12°, and the second member 22 is provided with angle indicia 662, for example, indicia representing 0-12°. By aligning the same angle indicia on the members 20, 22, here 9.0° is illustrated, the connector is set at the desired angulation. In use, to align vector 50 and axis, Z (FIG. 6A), the surgeon aligns the same angle indicia with a mark 664 on the bone surface 44; the mark 664 having previously been determined by the surgeon to correspond to the alignment point that produces the desired inclination and retroversion, as described above.

Figure 30:
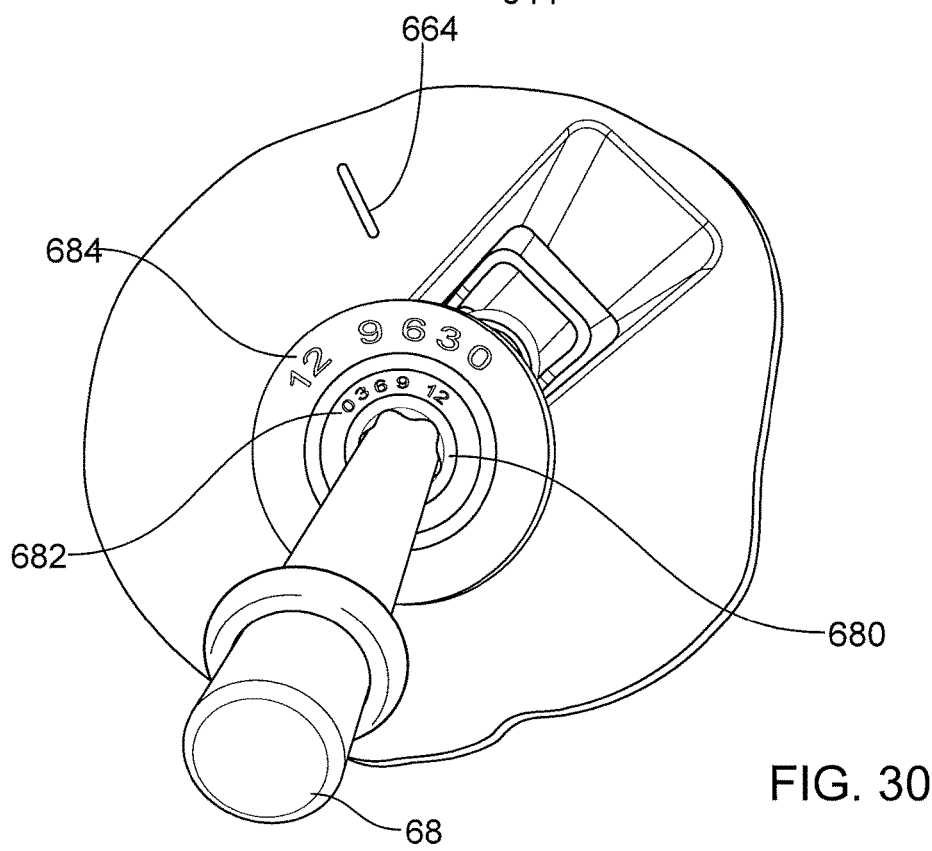
FIG. 30 illustrates another use of a trial connector.

Referring to FIG. 30, the surgeon can use a trial connector 680 to check that the angulation, length, and alignment mark 664 produce the desired result. FIG. 30 shows first and second members 682, 684 of the trial connector 680 aligned with each other at the angulation indicated by the mark 664. The surgeon can then select the second member 684 that provides the desired length indicated by the guide 110, 210, 300, couples a trial head component 594 (FIG. 25G) to the trial connector 680, and rotates the head 594 to a position that provides optimal coverage of the bone surface 44. The surgeon then takes the trial through a trial range of motion.

Referring again to FIGS. 31A and 31B, if the trial connector 680 provides the desired functionality, the surgeon selects a member 20 having the desired length and uses screw 18 to couple the member 20 to the stem 14. The surgeon rotates member 20 about axis, X, to align the indicia 660 corresponding to the desired angulation with the mark 664. The surgeon then tightens the screw 18 to fix the member 20 to the stem 14, slides the member 22 over the member 20, and rotates the member 22 to align the indicia 662 corresponding to the desired angulation with the corresponding indicia 660 on the member 20 and the mark 64. The surgeon then impacts the member 22 such that the tapers 24, 26 fix the member 22 to the member 20, slides the head 12 over the member 22, rotates the head 12 to the position that provides optimal coverage of the bone surface 44, and impacts the head 12 such that the tapers 28, 30 fix the head 12 to the member 22 (FIG. 2).

A number of implementations of the invention have been described. Nevertheless, it will be understood that various modifications may be made without departing from the spirit and scope of the invention. For example, the member 20 can be an integral component of the stem 14 that is not movable relative to the stem 14. Such an integral component would have more limited adjustability. The stem 14 itself can be a single integral component or the stem 14 can include a stem body 14*a* and a proximal body 14*b* (FIG. 3), which can be coupled to and rotatably adjusted relative to the stem body 14*a* prior to fixing the proximal body 14*b* to the stem body 14*a*. Additionally, rather than the first member 112, 212 and the second member 114, 214 rotating together relative to the stem 14 (FIGS. 14 and 15), the second member 114, 214 can rotate relative to the first member 112, 212. The wall 320 of FIG. 20C can have more or fewer quadrants and be able to tilt about more or fewer planes. The anatomic guide 110, 210, 300 is illustrated in use with a stem implanted in the humeral bone. However, the anatomic guide 110, 210, 300 can be used with implants in other bones.

Accordingly, other implementations are within the scope of the following claims.

What is claimed is:

1. A method of aligning a prosthetic stem and a prosthetic humeral head, the method comprising:
    placing the prosthetic stem in a humeral bone, followed by:
        coupling a first intermediate sleeve to a proximal end of the prosthetic stem, the first intermediate sleeve defining an opening having a central axis of the opening, wherein the first intermediate sleeve is configured to rotate about the central axis relative to the prosthetic stem, wherein the first intermediate sleeve has a male taper that is angularly offset relative to the central axis of the opening in the first intermediate sleeve;
        coupling a first alignment member to the first intermediate sleeve, the first alignment member having a disc-like configuration;
        rotating the first alignment member and the first intermediate sleeve as a unit to place the first intermediate sleeve in an alignment position;
        securing the first intermediate sleeve to the prosthetic stem with the first intermediate sleeve in the alignment position;
        removing the first alignment member from the first intermediate sleeve;
        coupling a second intermediate sleeve to the first intermediate sleeve, the second intermediate sleeve defining a second opening configured to receive the male taper of the first intermediate sleeve, wherein the second opening has a central axis about which the second intermediate sleeve is configured to rotate relative to the first intermediate sleeve, wherein the second intermediate sleeve has a male taper that is angularly offset relative to the central axis of the second opening through the second intermediate sleeve;
        coupling a second alignment member to the second intermediate sleeve, the second alignment member having a disc-like configuration;
        rotating the second intermediate sleeve relative to the first intermediate sleeve using the second alignment member to provide a desired orientation of the second intermediate sleeve;
        removing the second alignment member from the second intermediate sleeve; and
        securing the second intermediate sleeve to the prosthetic humeral head,
        wherein securing the second intermediate sleeve to the prosthetic humeral head comprises coupling the second intermediate sleeve to the prosthetic humeral head using the male taper such that an axis of rotation of the prosthetic humeral head with respect to the second intermediate sleeve is not aligned with the axis of rotation of the second intermediate sleeve with respect to the first intermediate sleeve.

2. The method of claim 1 wherein the first alignment member is coupled to the first intermediate sleeve without rotationally aligning the first alignment member relative to the first intermediate sleeve.

3. The method of claim 1 wherein the first intermediate sleeve includes an indicator.

4. The method of claim 1 wherein the first alignment member includes a plurality of indicia.

5. The method of claim 1 further comprising fixing the second intermediate sleeve to the first intermediate sleeve with the second intermediate sleeve in the desired orientation.

6. The method of claim 1 wherein the second alignment member is coupled to the second intermediate sleeve without rotationally aligning the second alignment member relative to the second intermediate sleeve.

7. The method of claim 1 wherein the second intermediate sleeve is in the desired orientation when the second alignment member is parallel to a bone osteotomy.

8. The method of claim 1 wherein the first intermediate sleeve is in the alignment position when the first alignment member is parallel to a bone osteotomy.

9. The method of claim 1 wherein rotating the second intermediate sleeve relative to the first intermediate sleeve using the second alignment member to provide a desired orientation of the second intermediate sleeve comprises:
    rotating the second alignment member and the second intermediate sleeve as a unit to place the second intermediate sleeve in the desired orientation.

10. The method of claim 1 wherein securing the second intermediate sleeve to the prosthetic humeral head comprises engaging the second intermediate sleeve with a side of the prosthetic humeral head that is opposite an articular surface of the prosthetic humeral head.

11. The method of claim 1 wherein securing the second intermediate sleeve to the prosthetic humeral head comprises securing the second intermediate sleeve to the prosthetic humeral head with a tapered connection between the second intermediate sleeve and the prosthetic humeral head.

12. The method of claim 1 wherein securing the second intermediate sleeve to the prosthetic humeral head comprises engaging a male taper of the second intermediate sleeve with a female taper of the prosthetic humeral head.

13. The method of claim 1 wherein coupling the second intermediate sleeve to the first intermediate sleeve comprises receiving a portion of the first intermediate sleeve in a female taper of the second intermediate sleeve; and
wherein securing the second intermediate sleeve to the prosthetic humeral head comprises receiving a male taper of the second intermediate sleeve in an opening of the prosthetic humeral head, wherein the male taper of the second intermediate sleeve extends around the female taper of the second intermediate sleeve.

14. The method of claim 1, wherein securing the second intermediate sleeve to the prosthetic humeral head comprises securing the second intermediate sleeve to the prosthetic humeral head such that a portion of the first intermediate sleeve is received in the second intermediate sleeve and in the prosthetic humeral head.

15. The method of claim 1 wherein coupling the second intermediate sleeve to the first intermediate sleeve comprises coupling, to the first intermediate sleeve, a second intermediate sleeve having a female taper that engages a male taper of the first intermediate sleeve such that an axis of rotation of the second intermediate sleeve with respect to the first intermediate sleeve is not aligned with an axis of rotation of the first intermediate sleeve with respect to the prosthetic stem.

16. The method of claim 1 wherein coupling the first alignment member to the first intermediate sleeve comprises receiving a portion of the first intermediate sleeve in an opening of the first alignment member.

17. The method of claim 1 wherein coupling the first alignment member to the first intermediate sleeve comprises coupling the first alignment member and the first intermediate sleeve such that the first alignment member is placed around an exterior circumference of the first intermediate sleeve.

18. The method of claim 1 wherein coupling the first alignment member to the first intermediate sleeve comprises engaging a portion of the first alignment member with a male taper of the first intermediate sleeve.

19. The method of claim 1, wherein the prosthetic stem defines an interface axis;
wherein rotating the first alignment member and the first intermediate sleeve as a unit comprises:
rotating the first alignment member and the first intermediate sleeve about the central axis of the opening in the first intermediate sleeve, wherein rotating the first alignment member and the first intermediate sleeve changes an angular orientation of the male taper relative to the prosthetic stem while the central axis of the opening substantially coincides with the interface axis of the prosthetic stem.

20. The method of claim 1, wherein the prosthetic stem defines an interface axis; and
wherein securing the first intermediate sleeve to the prosthetic stem comprises:
securing the first intermediate sleeve to the prosthetic stem with an interface that causes the central axis of the opening of the first intermediate sleeve to substantially coincide with the interface axis.

21. A method of aligning a prosthetic stem and a prosthetic humeral head, the method comprising:
placing the prosthetic stem in a humeral bone, followed by:
coupling a first intermediate sleeve to a proximal end of the prosthetic stem, the first intermediate sleeve defining an opening having a central axis of the opening, wherein the first intermediate sleeve is configured to rotate about the central axis relative to the prosthetic stem, wherein the first intermediate sleeve has a male taper that is angularly offset relative to the central axis of the opening in the first intermediate sleeve;
coupling a first alignment member to the first intermediate sleeve, the first alignment member having a disc-like configuration;
rotating the first alignment member and the first intermediate sleeve as a unit to place the first intermediate sleeve in an alignment position;
securing the first intermediate sleeve to the prosthetic stem with the first intermediate sleeve in the alignment position;
removing the first alignment member from the first intermediate sleeve;
coupling a second intermediate sleeve to the first intermediate sleeve, the second intermediate sleeve defining a second opening configured to receive the male taper of the first intermediate sleeve, wherein the second opening has a central axis about which the second intermediate sleeve is configured to rotate relative to the first intermediate sleeve, wherein the second intermediate sleeve has a male taper that is angularly offset relative to the central axis of the second opening through the second intermediate sleeve;
coupling a second alignment member to the second intermediate sleeve, the second alignment member having a disc-like configuration;
rotating the second intermediate sleeve relative to the first intermediate sleeve using the second alignment member to provide a desired orientation of the second intermediate sleeve;
removing the second alignment member from the second intermediate sleeve; and
coupling the second intermediate sleeve to the prosthetic humeral head, the prosthetic humeral head having a convex articular surface,
wherein securing the second intermediate sleeve to the prosthetic humeral head comprises coupling the second intermediate sleeve to the prosthetic humeral head using the male taper such that an axis of rotation of the prosthetic humeral head with respect to the second intermediate sleeve is not aligned with the axis of rotation of the second intermediate sleeve with respect to the first intermediate sleeve.

22. The method of claim 21 wherein the first alignment member is coupled to the first intermediate sleeve without rotationally aligning the first alignment member relative to the first intermediate sleeve.

23. A method of aligning a prosthetic stem and a prosthetic humeral head, the method comprising:
placing the prosthetic stem in a humeral bone, followed by:

coupling a first intermediate sleeve to a proximal end of the prosthetic stem, the first intermediate sleeve defining an opening having a central axis of the opening, wherein the first intermediate sleeve is configured to rotate about the central axis relative to the prosthetic stem, wherein the first intermediate sleeve has a male taper that is angularly offset relative to the central axis of the opening in the first intermediate sleeve;

coupling a first alignment member to the first intermediate sleeve by receiving a portion of the first intermediate sleeve in an opening of the first alignment member, the first alignment member having a disc-like configuration;

rotating the first alignment member and the first intermediate sleeve as a unit to place the first intermediate sleeve in an alignment position;

securing the first intermediate sleeve to the prosthetic stem with the first intermediate sleeve in the alignment position;

removing the first alignment member from the first intermediate sleeve;

coupling a second intermediate sleeve to the first intermediate sleeve, the second intermediate sleeve defining a second opening configured to receive the male taper of the first intermediate sleeve, wherein the second opening has a central axis about which the second intermediate sleeve is configured to rotate relative to the first intermediate sleeve, wherein the second intermediate sleeve has a male taper that is angularly offset relative to the central axis of the second opening through the second intermediate sleeve;

coupling a second alignment member to the second intermediate sleeve by receiving a portion of the second intermediate sleeve in an opening of the second alignment member, the second alignment member having a disc-like configuration;

rotating the second intermediate sleeve relative to the first intermediate sleeve using the second alignment member to provide a desired orientation of the second intermediate sleeve;

removing the second alignment member from the second intermediate sleeve; and coupling the second intermediate sleeve to the prosthetic humeral head, wherein securing the second intermediate sleeve to the prosthetic humeral head comprises coupling the second intermediate sleeve to the prosthetic humeral head using the male taper such that an axis of rotation of the prosthetic humeral head with respect to the second intermediate sleeve is not aligned with the axis of rotation of the second intermediate sleeve with respect to the first intermediate sleeve.

24. The method of claim 23 comprising:

while the second intermediate sleeve is in the desired orientation of the second intermediate sleeve, adjusting a position of the prosthetic humeral head by rotating the prosthetic humeral head relative to the second intermediate sleeve to place the prosthetic humeral head in an adjusted position; and securing the second intermediate sleeve to the prosthetic humeral head in the adjusted position of the prosthetic humeral head.

25. The method of claim 23 wherein coupling the second intermediate sleeve to the prosthetic humeral head comprises receiving a male taper of the second intermediate sleeve in a female taper of the prosthetic humeral head.

26. The method of claim 23 wherein coupling the second intermediate sleeve to the first intermediate sleeve comprises coupling, to the first intermediate sleeve, a second intermediate sleeve in which the opening in the second intermediate sleeve has a central axis about which the second intermediate sleeve is configured to rotate relative to the first intermediate sleeve, wherein the second intermediate sleeve has a male taper that is angularly offset relative to the central axis of the opening in the second intermediate sleeve.

\* \* \* \* \*